United States Patent [19]

Smith et al.

[11] Patent Number: 5,330,741
[45] Date of Patent: Jul. 19, 1994

[54] LONG-WAVELENGTH WATER SOLUBLE CHLORIN PHOTOSENSITIZERS USEFUL FOR PHOTODYNAMIC THERAPY AND DIAGNOSIS OF TUMORS

[75] Inventors: Kevin M. Smith; Shwn-Ji H. Lee, both of Davis, Calif.

[73] Assignee: The Regents of the University of California, Oakland, Calif.

[21] Appl. No.: 840,347

[22] Filed: Feb. 24, 1992

[51] Int. Cl.$^5$ .................... A61K 31/40; C07D 487/22
[52] U.S. Cl. ........................ 424/9; 514/410; 540/145
[58] Field of Search .................... 514/410; 424/9; 540/145

[56] References Cited

U.S. PATENT DOCUMENTS

| | | | |
|---|---|---|---|
| 4,675,338 | 6/1987 | Bommer et al. | 514/410 |
| 4,693,855 | 9/1987 | Bommer et al. | 424/2 |
| 4,977,177 | 12/1990 | Bommer et al. | 514/410 |

FOREIGN PATENT DOCUMENTS 0168831 1/1986 European Pat. Off. .

OTHER PUBLICATIONS

Roberts, W. G., et al., In Vitro Characterization of Monoaspartyl Chlorin $e_6$ and Diaspartyl Chlorin $e_6$ for Photodynamic Therapy, *J. Nat'l. Can. Inst.*, 80:330–336(1988).

Hoober, J. K., Photodynamic Sensitizers from Chlorophyll: Purpurin-18 and Chlorin $p_6$, *Photochem. Photobiol.*, 48:579–582(1988).

*Primary Examiner*—Richard L. Raymond
*Attorney, Agent, or Firm*—Hana Dolezalova

[57] ABSTRACT

Novel photosensitizers useful for photodynamic therapy and diagnosis of tumors. Photosensitizers are derived from chlorophyll-a of photosynthetic plants and algae, possess long wavelength absorption between 600 and 800 nm, are stable, and water soluble. A process of preparation of these compounds and method of use for diagnostic and therapeutic purposes.

26 Claims, 5 Drawing Sheets

Optical Spectrum of Chlorin-$p_6$-6-$N^6$-lysylamide-7-methyl Ester (II) in MeOH.

LCP

Optical Spectrum of Chlorin-$p_6$-6-N-Butylamide-$\gamma$-7-dimethyl Ester (IX) in $CH_2Cl_2$ N-BUTYL-CHLORIN-P6-MAJOR/$CH_2Cl_2$ Optical Spectrum of Chlorin-$p_6$-6-$N^6$-lysylmethoxyamide-7-methyl Ester (III) in $CH_2Cl_2$ LCP-LYS-ME/$CH_2Cl_2$ Optical Spectrum of Chlorin-$p_6$ $\gamma$-$N^6$-lysylmethoxyamide-7-methyl Ester (IV) in $CH_2Cl_2$ LCP-LYS-ME/$CH_2Cl_2$

LONG-WAVELENGTH WATER SOLUBLE CHLORIN PHOTOSENSITIZERS USEFUL FOR PHOTODYNAMIC THERAPY AND DIAGNOSIS OF TUMORS

The present invention was made in the course of research supported by the research grant CHE-86-19034 from the National Science Foundation. The United States Government may have certain rights in this invention.

BACKGROUND OF THE INVENTION

1. Field of Invention

This invention concerns novel photosensitizing compounds useful for photodynamic therapy and diagnosis of tumors. In particular, the invention concerns photosensitizers which are derived from photosynthetic plants and algae, which possess long wavelength absorption between 600 and 700 nm, which are water soluble and which are useful for diagnostic tumor localization and photodynamic therapy of tumors. The invention further concerns the process of preparation of these compounds and method of use, both for diagnostic and therapeutic purposes.

BACKGROUND ART AND RELATED ART DISCLOSURES

Photodynamic therapy (PDT) is a new approach to cancer diagnosis and therapy. PDT involves systemic administration of a photosensitizer, a photosensitive compound which in itself is essentially therapeutically inactive, followed by illumination of the lesion or tumor with visible light. PDT has been first described in *Cancer Res.*, 38:2628 (1976) and since 1976, photodynamic therapy has been used experimentally in cancer patients with an estimated 3,000–4,000 patients treated worldwide. PDT is based on findings published in *J. Natl. Cancer Inst.*, 26:1 (1961) that a derivatized hematoporphyrin (HpD) which has fluorescent properties is selectively uptaken by malignant tissue tissue. Subsequently, studies described in *Ann. Surg.*, 167:829 (1968) indicated that HpD was taken up by a wide variety of carcinomas and sarcomas both in man and animals. The therapeutic potential of HpD as an in situ photosensitizing agent was first disclosed in *Proc. IX Internat. Cancer Congr.*, 393 (1966) and actually used for treatment with light of a patient with metastatic breast cancer following injection of HpD. A positive tumor response to this treatment was observed.

In 1975, *J. Natl. Cancer Inst.*, 55:115 (1975) reported that a transplanted mammary tumor in mice could be eradicated completely using filtered red light following systemic injection of HpD and about the same time, a positive tumor response to a treatment of a bladder tumor was described in a patient injected with HpD by delivering light endoscopically via a glass light guide. In response to the treatment, the tumor size decreased in the treated area with no apparent effect in the untreated area. These findings were reported in *J. Urol.*, 155:150 (1976). Since that time, numerous clinical trials using HpD have been reported encompassing essentially all solid tumors accessible on the skin surface or endoscopically.

So far, several groups of compounds are known to act as photosensitizers. HpD, available as Photofrin I and its more purified version Photofrin II are the first clinical photosensitizers developed by Quadra Logic Technologies and Lederle Laboratories. They are prepared by acid catalyzed acetylation of hematoporphyrin (Hp) and subsequent alkaline treatment. These compounds are complex oligomeric mixtures contaminated with starting hematoporphyrin and its dehydration products. The oligomeric mixtures which comprise 50 to 80% of the tumor-localizing fraction of HpD are selectively retained in the tumors and are responsible for both the in vivo fluorescence and for photosensitizing properties of HpD.

In spite of the potential broad diagnostic and therapeutic application of PDT in clinical oncology, there are disadvantages connected with use of HpD because of the lack of a complete understanding of which active component or components in the HpD complex are responsible for tumor uptake and retention. Moreover, the limited tumor selectivity of HpD, the limited tissue penetration of the light upon treatment following HpD administration by systemic injection and limited retention by malignant tissues were observed.

Photodynamic treatment with porphyrins is further complicated by observation that normal nontumorous organs such as liver, kidney, spleen and skin tend to retain considerable amounts of the porphyrins which upon light illumination react as it does in the tumor tissue, that is by probably producing cytotoxic singlet oxygen which affects normal tissue, causing undesirable side effects. Skin photosensitivity also becomes a problem associated with this treatment since a patient must remain in subdued light for four to six weeks after HpD administration to avoid cutaneous phototoxicity.

The other major drawback of HpD is its weak absorbance at 630 nm, the wavelength of red light most commonly used in PDT. Incomplete responses to the HpD treatment in some cases were attributed to the difficulty in delivering light to some tumor sites and to incomplete light penetration for larger tumors due to its weak absorbance.

These problems have resulted in considerable efforts devoted to developing new photosensitizers having increased absorption maxima in the 600–800 nm region in order to increase the efficiency of the light as well as to achieve greater tissue penetration with the longer wavelengths.

Several new classes of photosensitizers for use in PDT are derived from tetrapyroles and their derivatives. Tetrapyrolic macrocycles are the most ubiquitous of all naturally occurring pigments and most of them generate high quantum yields of triplet states from which energy transfer to ground state oxygen appears to be the most dominant process. Synthetic etiopurpurin, benzochlorines, rhodins, verdins, and methyl pyrroverdin as well as the novel pentapyrolic macrocycles pentaphyrin and sapphyrin have shown very promising results in PDT, and are considered to be a new generation of PDT photosensitizers. While these compounds seem to possess absorption wavelength maxima around 750–800 nm, some of these compounds are highly unstable and thus not overly suitable and practical for diagnostic and therapeutic purposes.

Tetrapyrrole compounds and a process for the production of thereof useful in photodiagnosis and phototherapy is described in the EPO patent application 85108981.3 filed on Jul. 18, 1985.

Phthalocyanines and their derivatives are another class of new photosensitizers under investigation. They are structurally related to the naturally occurring porphyrins but have the four isoindole units linked by azanitrogens rather than methane linkages. These compounds show strong absorption in the 650-700 nm range, and certain non-metallo as well as metallo derivatives exhibit efficient photochemical processes. However, since the most studied sulfonated phthalocyanines are composed of mono-, di-, tri- and tetrasulfonated species, they may not be the most suitable for human use.

So far the most promising new (second generation) photosensitizer closest to the clinic is mono-L-aspartyl-chlorin e6 (MACE) and a related compound Di-L-aspartyl-chlorin-e6 (DACE) which possess strong absorption bands with high molar extinction coefficients around 664 nm. MACE and DACE are prepared by alkaline degradation from methyl pheophorbide-a followed by esterification with diazomethane to give chlorin e6 trimethyl ester, which is then converted to the acid chloride. Aspartic acid is then added using usual peptide chemistry.

Initial PDT experiments demonstrated that MACE was ineffective at inducing tumor cures when a 24 hours time interval between drug administration and light treatment was used. However, when MACE was administered 4-6 hours prior to light exposure, PDT induced tumor cures were obtained. In addition, the level of PDT induced normal skin damage was significantly lesser for MACE than for HpD at comparable drug and light doses. The results of testing indicated that MACE is a short-acting but not overly effective tumor photosensitizer with good in vivo clearance properties. The characterization of MACE and DACE is described in *J. Natl. Cancer Inst.*, 80:330 (1988).

Purpurin-18 and chlorin-p6, two derivatives of chlorophyll, described in *Photochemistry and Photobiology*, 48:579 (1988) are potent photosensitizers which promote cell killing by low intensity of red light.

All patents, patent application and publications cited herein are hereby incorporated by reference in their entirety.

Current invention provides a group of new chlorin-p6 photosensitizers which are derivatives of chlorophyll-a. These new photosensitizers are stable water soluble compounds which are easy to synthesize. They have enhanced molar extinction and electronic absorption peaks at longer wavelengths than HpDs and other known photosensitizers allowing for increased tissue penetration and tumor photodestruction. They are shorter acting and do not cause severe cutaneous photosensitization after 24 hours or other side effects.

SUMMARY

One aspect of the current invention are the new chlorin photosensitizers which are derivatives of chlorophyll-a.

Another aspect of the current invention are chlorin p6 photosensitizers which are 7,8-dihydroporphyrins derived naturally from photosynthetic plants and algae.

Still another aspect of the current invention are chlorin p6 photosensitizers derived from *Spirulina maxima* alga which contains large amounts of chlorophyll-a from which methyl pheophorbide-a is extracted and degraded to purpurin-18 methyl ester, a precursor of the current compounds, from which the current chlorin photosensitizers are prepared by opening its anhydride ring with amino groups in amino acids, amines, nucleotides or with oxygen functionalities in alcohols.

Yet another aspect of the current invention is a photosensitizer which is a lysyl chlorin p6.

Still yet another aspect of the current invention is a method for photodynamic diagnosis and therapy of tumors by administering to a patient suffering from a tumor a sufficient amount of a photosensitizer of the current invention subsequently followed by light irradiation having appropriate wavelength achieving a maximal photosensitization.

Yet another aspect of the current invention are compounds of the formula

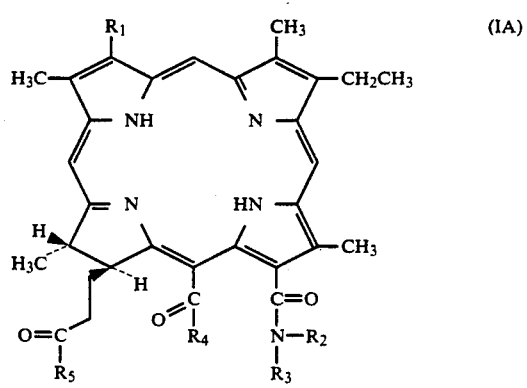

(IA)

wherein $R_1$ is H; $CH_3$; $CH_2CH_3$; $CH=CH_2$; $CH(OH)CH_3$; $CH(O\text{-alkyl})CH_3$; $C(=O)CH_3$; CHO; $CH_2OH$; or $CH_2$-alkoxy;

$R_2$ is H; alkyl; aryl;

$R_3$ is H; alkyl; aryl; $CH(R_6)CO_2H$ where $R_6$ is any natural amino acid side-chain; $CH(R_7)CO_2R_8$ where $R_7$ is any natural amino acid side-chain, and $R_8$ is alkyl, aryl; $(CH_2)_nCH(NH_2)CO_2H$ wherein n is 3 or 4; aryl substituted on aromatic ring with alkyl; alkyl substituted with $N(alkyl)_2$, $N^+(alkyl)_3$; $(CH_2)_nCO_2R_9$; and where $R_9$ is H, alkyl or aryl;

$R_4$ is OH; alkoxy;

$R_5$ is OH; $OR_{10}$ wherein $R_{10}$ is alkyl or aryl; $NHR_{11}$ wherein $R_{11}$ is alkyl or aryl; $NR_{12}R_{13}$ wherein $R_{12}$ and $R_{13}$ are H, alkyl or aryl; $NHCH(R_{14})CO_2H$ wherein $R_{14}$ is any natural amino acid side-chain); $NHCH(R_{15})CO_2R_{16}$ wherein $R_{15}$ is any natural amino acid side-chain, and $R_{16}$ is alkyl or aryl; or $NH(CH_2)_nCH(NH_2)CO_2H$ wherein n is 3 or 4 or

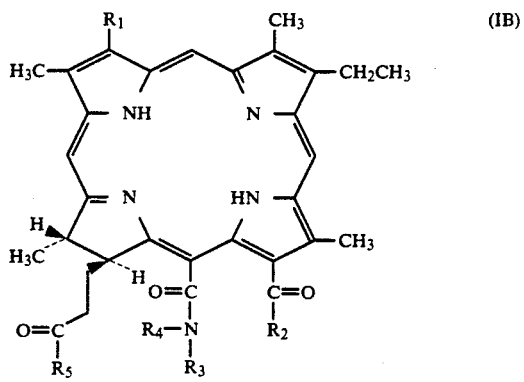

(IB)

wherein $R_1$ is H; $CH_3$; $CH_2CH_3$; $CH=CH_2$; $CH(OH)CH_3$; $CH(O\text{-alkyl})CH_3$; $C(=O)CH_3$; $CH_2OH$; or $CH_2$-alkoxy;

$R_2$ is OH; alkoxy;

$R_3$ is H; alkyl; aryl;

$R_4$ is H; alkyl; aryl; $CH(R_6)CO_2H$ where $R_6$ is any natural amino acid side-chain; $CH(R_7)CO_2R_8$ where $R_7$ is any natural amino acid side-chain, and $R_8$ is alkyl, aryl; $(CH_2)_nCH(NH_2)CO_2H$ wherein n is 3 or 4; aryl substituted on aromatic ring with alkyl; alkyl substituted with $N(alkyl)_2$ or $^{(+)}N(alkyl)_3$; $(CH_2)_nCO_2R_9$; and where $R_9$ is H, alkyl or aryl;

$R_5$ is OH; $OR_{10}$ wherein $R_{10}$ is alkyl or aryl; $NHR_{11}$ wherein $R_{11}$ is alkyl or aryl; $NR_{12}R_{13}$ wherein $R_{12}$ and $R_{13}$ are H, alkyl or aryl; $NHCH(R_{14})CO_2H$ wherein $R_{14}$ is any natural amino acid side chain; $NHCH(R_{15})CO_2R_{16}$ wherein $R_{15}$ is any natural amino acid side-chain, and $R_{16}$ is alkyl or aryl; or $NH(CH_2)_nCH(NH_2)CO_2H$ wherein n is 3 or 4.

Still another aspect of the current invention is a process for preparation of these compounds by opening the anhydride ring of purpurin-18 methyl ester with amino group of the amino acids, amines, nucleotides, and with oxygen functionalities in alcohols.

Still another aspect of the current invention is a process for preparing novel chlorin photosensitizers by opening purpurin-18 methyl ester anhydride ring with lysine, lysine methyl ester, n-butylamine, methanol, or ornithine.

DETAILED DESCRIPTION OF THE INVENTION

Figure 1:
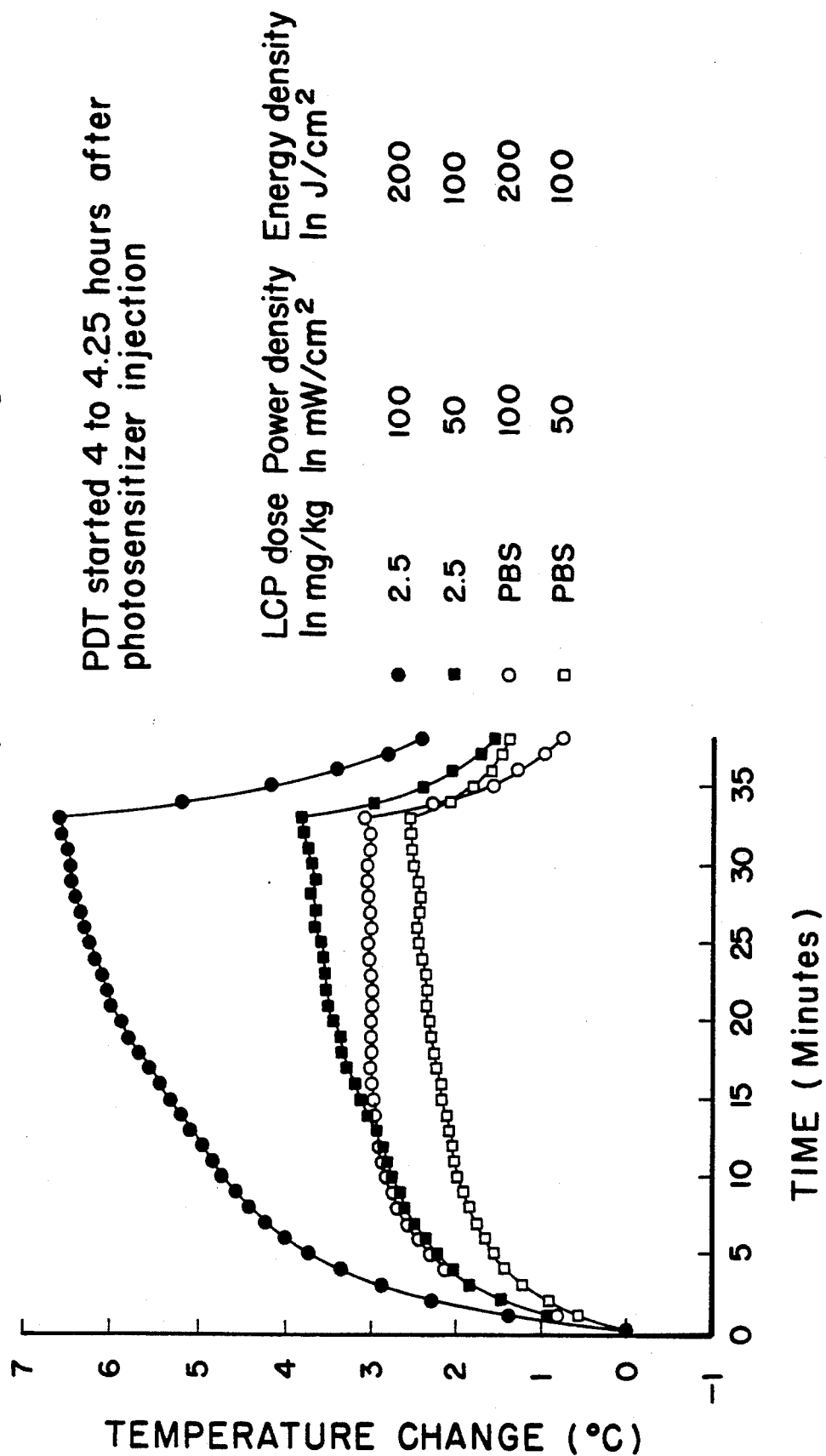
FIG. 1 illustrates light induced temperature change in rat glioma during the photodynamic therapy.

The current invention concerns novel type of photosensitizers derived from chlorophyll-a. These new photosensitizers are chlorophyll-a derivatives which are 7,8-dihydroporphyrins having opened their anhydride rings with the amino group from amino acids, amines, and with oxygen groups of alcohols. These derivatives possess long wavelength absorption maxima between 600 and 800 nm, are stable, water soluble fast acting and their preparation is easy and inexpensive as they are derived naturally from photosynthetic chlorophylis of plants and algae.

These novel compounds are selectively taken up by a variety of tumors and their absorption spectra maxima allow the irradiation of these tumors with the red light within the absorption spectra limits without affecting the other tissue. The light irradiation provokes an oxidation process sensitized by the photosensitizer producing cytotoxic singlet oxygen which effectively destroys tumorous cells. These features are extremely important for photodynamic diagnosis and therapy of tumors treated with novel photosensitizers of this invention. Fluorescence spectroscopy also allows diagnosis of tumors.

The invention is very practical as it allows relatively inexpensive synthesis of these new photosensitizers from naturally abundant chlorophyll containing plants and algae, by the simple process of opening the anhydride ring of the purpurin-18 derivative of chlorophyll with amino groups of amino acids, amines, nucleotides, or with oxygen functionalities in alcohols, or other compounds.

Sources for preparation of the compounds of the current invention are naturally occurring plants and algae containing chlorophyll, particularly chlorophyll-a.

Plants usually produce and contain both chlorophyll-a and chlorophyll-b in a ratio of about 3:1. Since for purposes of this invention, chlorophyll-a is preferred because it provides large amounts of a purpurin-18 methyl ester, a precursor for current compounds, commercially available algae *Spirulina maxima* alga which contains solely chlorophyll-a is an excellent, naturally occurring, plentiful, and inexpensive source for the synthesis of compound of the current invention.

The photosensitizers of the current invention are typically synthesized by the reactions illustrated in Reaction Scheme 1.

REACTION SCHEME 1

Spirulina Maxima Alga

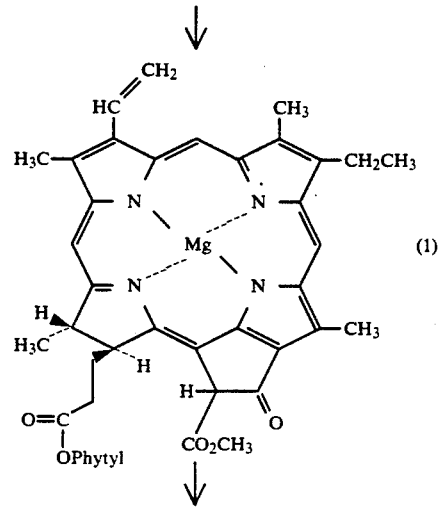

(1)

-continued
REACTION SCHEME 1

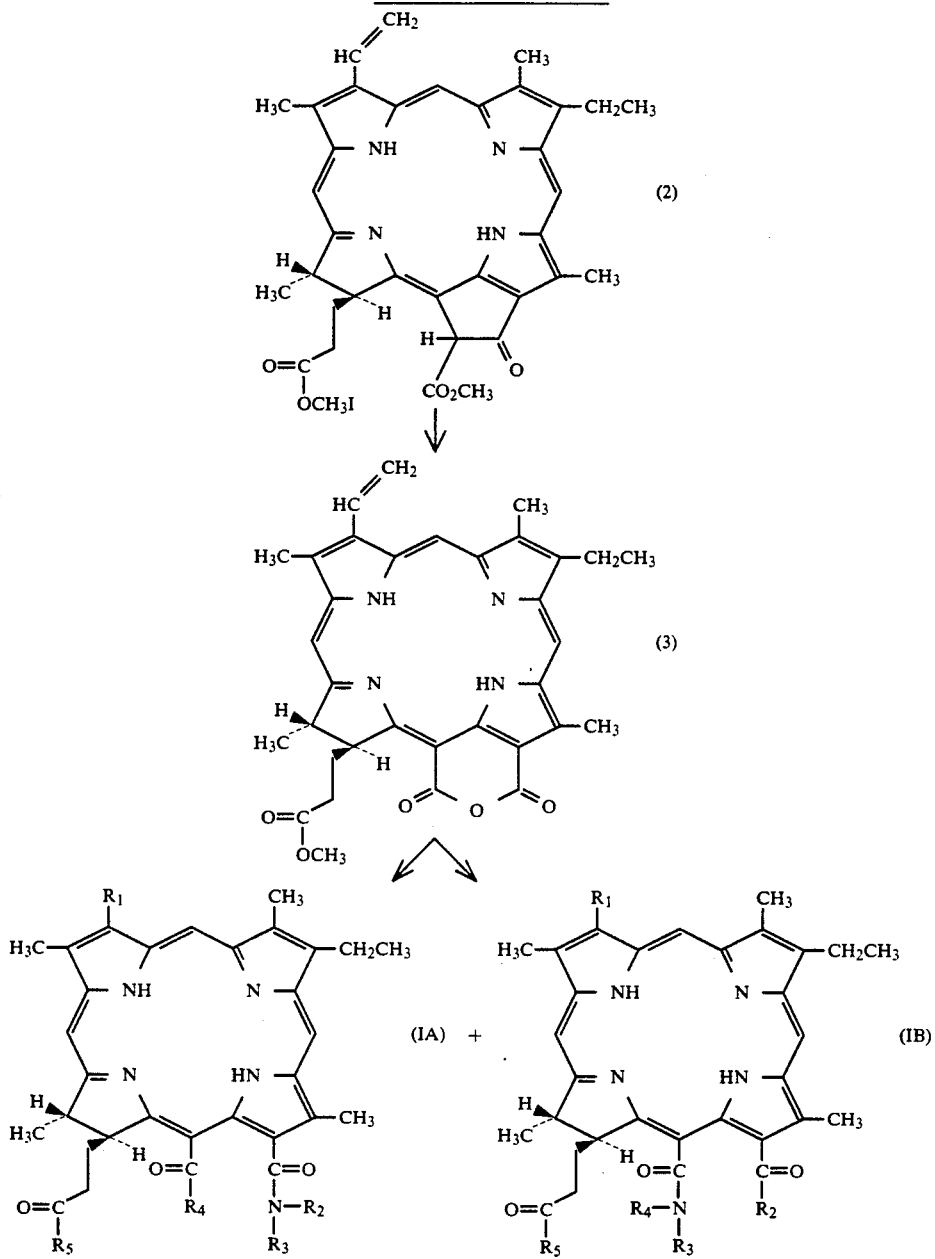

wherein, for (IA), $R_1$ is H; $CH_3$; $CH_2CH_3$; $CH=CH_2$; $CH(OH)CH_3$; $CH(O\text{-alkyl})CH_3$; $C(=O)$ $CH_3$; CHO; $CH_2OH$; alkoxy;

$R_2$ is H; alkyl; aryl;

$R_3$ is H; alkyl; aryl; $CH(R_6)CO_2H$ where $R_6$ is any natural amino acid side-chain); $CH(R_7)CO_2R_8$ where $R_7$ is any natural amino acid side-chain, and $R_8$ is alkyl, aryl; $(CH_2)_nCH(NH_2)CO_2H$ wherein n is 3 or 4; aryl substituted on aromatic ring with alkyl; alkyl substituted with $N(\text{alkyl})_2$, $(+)N(\text{alkyl})_3$; $(CH_2)_nCO_2R_9$; and where R is H, alkyl or aryl;

$R_4$ is OH; alkoxy;

$R_5$ is OH; $OR_{10}$ wherein $R_{10}$ is alkyl or aryl; $NHR_{11}$ wherein $R_{11}$ is alkyl or aryl; $NR_{12}R_{13}$ wherein $R_{12}$ and $R_{13}$ are H, alkyl or aryl; $NHCH(R_{14})CO_2H$ wherein $R_{14}$ is any natural amino acid side-chain); $NHCH(R_{15})CO_2R_{16}$ wherein $R_{15}$ is any natural amino acid side-chain, and $R_{16}$ is alkyl or aryl; or $NH(CH_2)_nCH(NH_2)CO_2H$ wherein n is 3 or 4;

and wherein, for (IB), $R_1$ is H; $CH_3$; $CH_2CH_3$; $CH=CH_2$; $CH(OH)CH_3$; $CH(O\text{-alkyl})CH_3$; $C(=O)$ $CH_3$; CHO; $CH_2OH$; $CH_2\text{alkoxy}$;

$R_2$ is OH; alkoxy;

$R_3$ is H; alkyl; aryl;

$R_4$ is H; alkyl; aryl; $CH(R_6)CO_2H$ where $R_6$ is any natural amino acid side-chain); $CH(R_7)CO_2R_8$ where $R_7$ is any natural amino acid side-chain, and $R_8$ is alkyl, aryl; $(CH_2)_nCH(NH_2)CO_2H$ wherein n is 3 or 4; aryl substituted on aromatic ring with alkyl; alkyl substituted with $N(\text{alkyl})_2$, $(+)N(\text{alkyl})_3$; $(CH_2)_nCO_2R_9$; and where R is H, alkyl or aryl;

$R_5$ is OH; $OR_{10}$ wherein $R_{10}$ is alkyl or aryl; $NHR_{11}$ wherein $R_{11}$ is alkyl or aryl; $NR_{12}R_{13}$ wherein $R_{12}$ and $R_{13}$ are H, alkyl or aryl; NHCH($R_{14}$)CO$_2$H wherein $R_{14}$ is any natural amino acid side-chain); NHCH($R_{15}$)CO$_2R_{16}$ wherein $R_{15}$ is any natural amino acid side-chain, and $R_{16}$ is alkyl or aryl; or NH(CH$_2$)$_n$CH(NH$_2$)CO$_2$H wherein n is 3 or 4.

Reaction Scheme 1 illustrates the general route of synthesis of the compound of the current invention starting with *Spirulina maxima* alga. *Spirulina maxima* alga contains solely chlorophyll-a (1) which can be easily extracted and transformed into a number of pur-purins, such as purpurin-7 and purpurin-18 methyl ester, through the chlorophyll-a degradation product methyl pheophorbide-a. Methyl pheophorbide-a (2) provides access to a large variety of potentially useful degradation products, such as purpurins by way of the allomerization reaction according to a method described in *J. Amer. Chem. Soc.*, 107:4946 (1985).

As seen in Reaction Scheme 1, chlorophyll-a, compound (1) and methyl pheophorbide-a, compound (2), are derived from and obtained by extraction from *Spirulina maxima* alga by methods described in *J. Amer. Chem. Soc.*, 107:4946 (1985). By opening the anhydride ring of purpurin-18 methyl ester (3) the compounds (IA) and (IB) as defined above are prepared.

Preparation of Purpurin-18 Methyl Ester (3)

Compound (3), purpurin-18, methyl ester, is prepared as follows.

Purpurin-18 methyl ester, compound (3), was prepared by treating methyl pheophorbide-a (2) in an alkaline solution, preferably in a mixture containing potassium hydroxide/n-propanol/ethyl ether in the presence of oxygen. The aerial oxidation of the enolate ion of methyl pheophorbide-a (2) resulted in cleavage of the C(9)-C(10) bond, and affords, after acidification with dilute acid, such as hydrochloric, phosphoric or preferably sulfuric acid, the product called "unstable chlorin". Acidification which proceeds in the range of pH 4-5 is critical for the next extraction step and for the yield. Over-acidification was found to result in low yields. The "unstable chlorin" was converted, upon repeated evaporation and redissolution in tetrahydrofuran, into purpurin-18. Incomplete conversion in this step caused the formation of purpurin-7 trimethyl ester, which was not desirable.

To obtain purpurin-18 methyl ester (3), purpurin 18 was esterified with ethereal diazomethane and the solution was washed with water before purification. Purification on preparative silica gel TLC plates yielded around 50% of purpurin-18-methyl ester (3). The optical spectrum of purpurin-18 methyl ester has its maximum absorption peak at 700 nm. Purpurin-18 and chlorin-p$_6$ have been previously known to be active in photodynamic therapy in in vitro conditions.

Novel Photosensitizers And Their Preparation

The novel photosensitizers compounds (IA) and (IB) are derivatives of chlorin-p$_6$, preferably a lysyl derivative, obtained by opening of anhydride ring of purpurin-18 methyl ester with amino group in amino acids, amines, nucleotides, or the oxygen in alcohol. These compounds are very active photosensitizers useful for treatment and diagnosis of various tumors.

The compounds have general formula

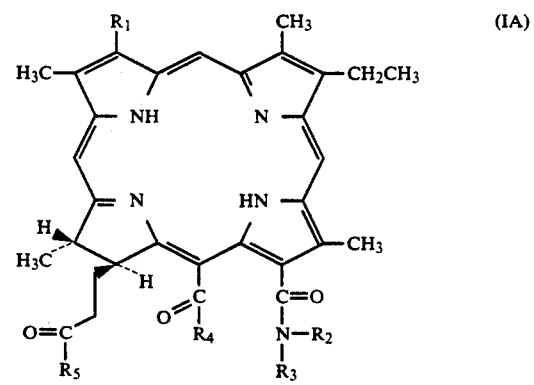

(IA)

wherein $R_1$ is H; CH$_3$; CH$_2$CH$_3$; CH=CH$_2$; CH(OH)CH$_3$; CH(O-alkyl)CH$_3$; C(=O)CH$_3$; CHO; CH$_2$OH; CH$_2$-alkoxy;

$R_2$ is H; alkyl; aryl;

$R_3$ is H; alkyl; aryl; CH($R_6$)CO$_2$H where $R_6$ is any natural amino acid side-chain); CH($R_7$)CO$_2R_8$ where $R_7$ is any natural amino acid side-chain, and $R_8$ is alkyl, aryl; (CH$_2$)$_n$CH(NH$_2$)CO$_2$H wherein n is 3 or 4; aryl substituted on aromatic ring with alkyl; alkyl substituted with N(alkyl)$_2$, +N(alkyl)$_3$; (CH$_2$)$_n$CO$_2R_9$; and where R is H, alkyl or aryl;

$R_4$ is OH; alkoxy;

$R_5$ is OH; OR$_{10}$ wherein $R_{10}$ is alkyl or aryl; NHR$_{11}$ wherein $R_{11}$ is alkyl or aryl; NR$_{12}R_{13}$ wherein $R_{12}$ and $R_{13}$ are H, alkyl or aryl; NHCH($R_{14}$)CO$_2$H wherein $R_{14}$ is any natural amino acid side-chain); NHCH($R_{15}$)CO$_2R_{16}$ wherein $R_{15}$ is any natural amino acid side-chain, and $R_{16}$ is alkyl or aryl; or NH(CH$_2$)$_n$CH(NH$_2$)CO$_2$H wherein n is 3 or 4.

The compounds may also have the general formula

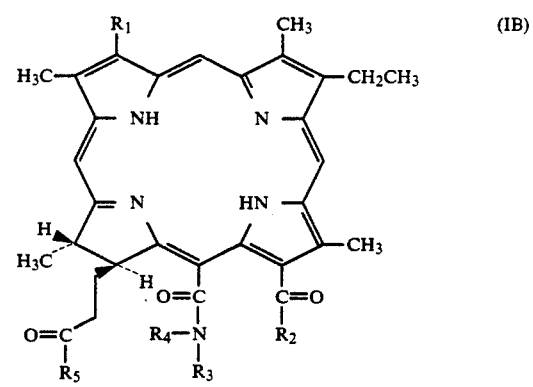

(IB)

wherein $R_1$ is H; CH$_3$; CH$_2$CH$_3$; CH=CH$_2$; CH(OH)CH$_3$; CH(O-alkyl)CH$_3$; C(=O)CH$_3$; CHO; CH$_2$OH; CH$_2$-alkoxy;

$R_2$ is H; alkyl; aryl;

$R_4$ is H; alkyl; aryl; CH($R_6$)CO$_2$H where $R_6$ is any natural amino acid side-chain); CH($R_7$)CO$_2R_8$ where $R_7$ is any natural amino acid side-chain, and $R_8$ is alkyl, aryl; (CH$_2$)$_n$CH(NH$_2$)CO$_2$H wherein n is 3 or 4; aryl substituted on aromatic ring with alkyl; alkyl substituted with N(alkyl)$_2$, +N(alkyl)$_3$; (CH$_2$)$_n$CO$_2R_9$; and where $R_9$ is H, alkyl or aryl;

$R_5$ is OH; $OR_{10}$ wherein $R_{10}$ is alkyl or aryl; $NHR_{11}$ $R_{11}$ is alkyl or aryl; $NR_{12}R_{13}$ $R_{12}$ and $R_{13}$ are H, alkyl or aryl; $NHCH(R_{14})CO_2H$ wherein $R_{14}$ is any natural amino acid side-chain; $NHCH(R_{15})CO_2R_{16}$ wherein $R_{15}$ is any natural amino acid side-chain, and $R_{16}$ is alkyl or aryl; or $NH(CH_2)_nCH(NH_2)CO_2H$ wherein n is 3 or 4.

Purpurin-18 Methyl Ester Anhydride Ring Opening by Lysine

Purpurin-18 methyl ester (3) anhydride ring opening with lysine results in the photosensitizer (II) having the formula:

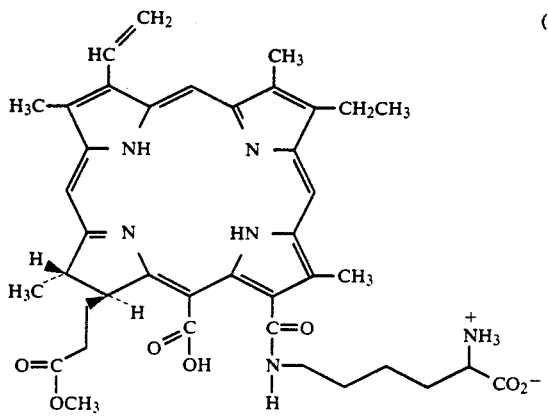

(II)

namely chlorin-p₆ 6-N$^\epsilon$-lysylamide-7-methyl ester compound (II).

Typically, during the anhydride ring opening procedure, purpurin-18 methyl ester (3) was dissolved first in methylene chloride followed by addition of aqueous lysine solution. The resulting two-layer mixture was diluted with pyridine which served as a weak base as well as helping to achieve homogeneity of the solution. After three days stirring at room temperature the formation of compound (II) was checked with high performance liquid chromatography (HPLC). HPLC showed about 80% consumption of purpurin-18 methyl ester (3) and also showed that the longer reaction proceeds, the more peaks appear.

Purpurin-18 methyl ester was dissolved in an excess amount of methylene chloride until it was completely dissolved. The solvent was then removed under vacuum using a Rotovapor. The dried purpurin-18 methyl ester adhered to the surface of the flask. Pyridine was then added to the flask while there was still some methylene chloride moisture present. In this way purpurin-18 methyl ester was easily dissolved in pyridine. Aqueous lysine solution was then added dropwise. Because of the insolubility of lysine in pyridine and purpurin-18 methyl ester in water, a small amount of pyridine or water was added to prevent either one from precipitating. The resulting reaction mixture was homogeneous and concentrated. According to spectrophotometry, the reaction was complete after 12 hours. HPLC of the crude mixture showed essentially only one peak.

Then, solvents were removed under high vacuum at temperatures below 40° C. and methylene chloride was added and evaporated to help remove the trace amount of residual pyridine. The crude product was dissolved in a small amount of water and transferred with a pipet to a syringe attached to a reversed phase HPLC $C_{18}$ SepPak cartridge (obtained from Waters Associates) and the aqueous solution was passed through the $C_{18}$ SepPak cartridge by gravity. When using the $C_{18}$SepPak cartridge with aqueous samples, it was necessary to pre-wet the cartridge with a water-miscible solvent such as methanol, acetonitrile, etc., and then with clean water. The required green product, which is less polar than lysine, stayed in the cartridge while lysine which is more polar was washed out with water. The cartridge was eluted with water and the presence of lysine was determined by a dilute solution of ninhydrin and collidine in 95% ethanol. Amino acids with a primary amino group react with ninhydrin and produce a violet colored dye which is detectable. The elution continued until all lysine was removed.

The polarity of the elution solvent was decreased gradually by increasing the concentration of methanol in 10% steps. The green product was eluted with 80:20 of methanol:water, and solvent was removed from the filtrate by freeze-drying. Attempts to remove all the solvents using a Rotovapor and heat caused regeneration of purpurin-18 methyl ester (3).

The resulting chlorin-p₆-7-N$^\epsilon$-lysylamide-7-methyl ester, compound (II), was found to be well soluble in water as required for easy administration of photosensitizer under in vitro and in vivo situations.

Figure 2:
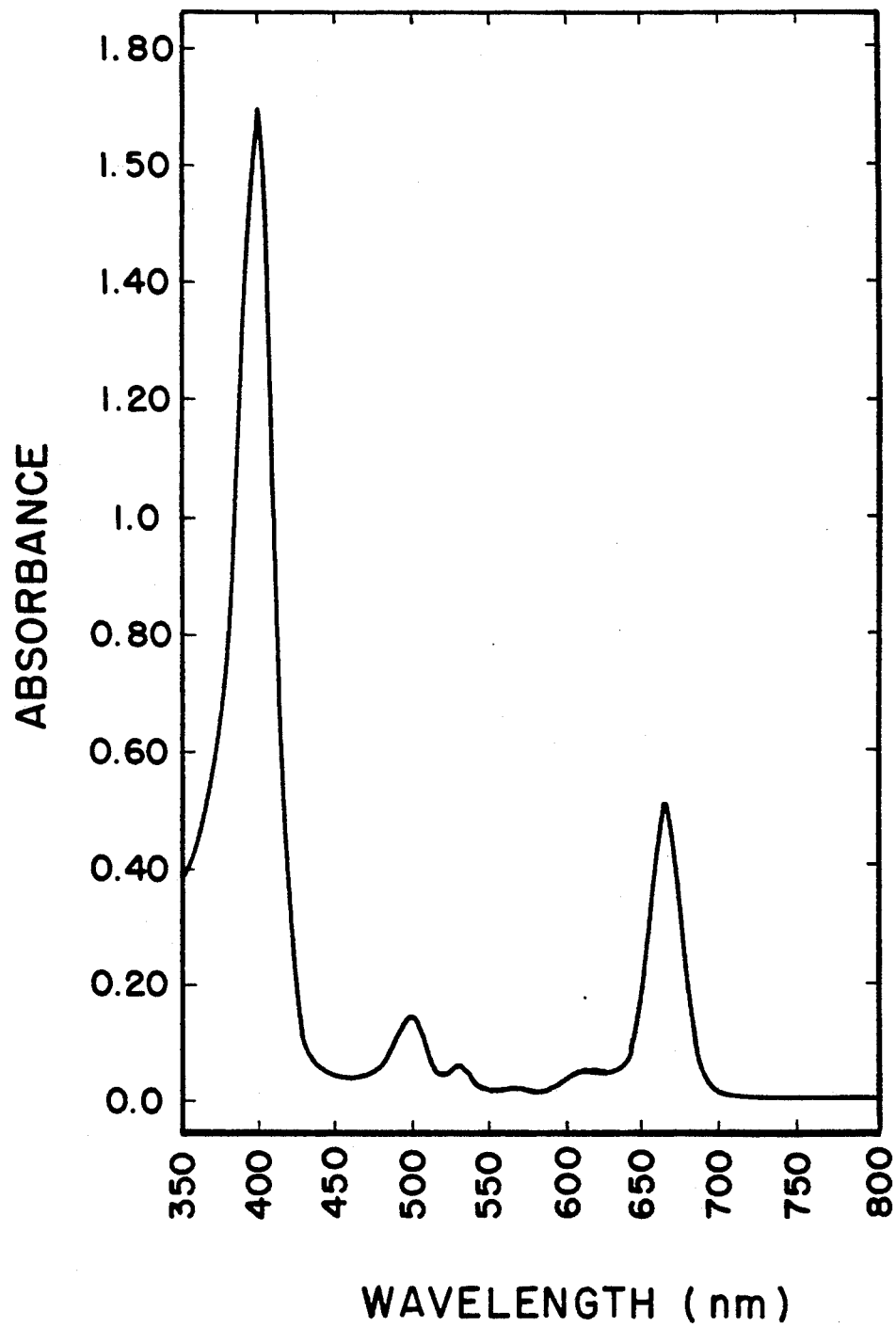
FIG. 2 is optical spectrum of chlorin-$p_6$-6-$N^\epsilon$-lysylamide-7-methyl ester in methanol.

The optical spectrum of chlorin-p₆-6-N$^\epsilon$-lysylamide-7-methyl ester (II) in methanol, seen in FIG. 2, showed the chlorin-p₆ absorption pattern. As seen from FIG. 2, the maximum absorbance appeared at about 670 nm wavelength. The reversed phase HPLC confirmed the presence of only one peak.

Purpurin-18 Methyl Ester Anhydride Ring Opening by Lysine Methyl Ester

A small amount of lysine methyl ester.2HCl was dissolved in 5 ml of water followed by addition of two equivalents of sodium hydroxide. Lysine methyl ester.2HCl was thereby neutralized with the two equivalents of sodium hydroxide followed by extraction into $CHCl_3$. Drying over $Na_2SO_4$ resulted in loss of most of the lysine methyl ester. The combined organic layer without drying was then evaporated under vacuum at temperatures below 40° C. to avoid dimerization to diketopiperazine. The resulting lysine methyl ester syrup was added slowly into a $CHCl_3$ solution of purpurin-18 methyl ester (3). The reaction was completed within one hour as determined by spectrophotometry and TLC. The reaction mixture was poured into a mixture of water and methylene chloride. The aqueous layer was slowly acidified to pH~6 by addition of dilute HCl to protonate the lysine methyl ester. Over-acidification regenerated a high percentage of purpurin-18 methyl ester. After removal of most of the lysine methyl ester by washing, the crude product was dried, the solvent was removed, and the product was purified on preparative silica gel TLC plates. Two green bands were isolated with a ratio of about ten to one.

These two bands corresponded to two compounds (III) and (IV) of formulas:

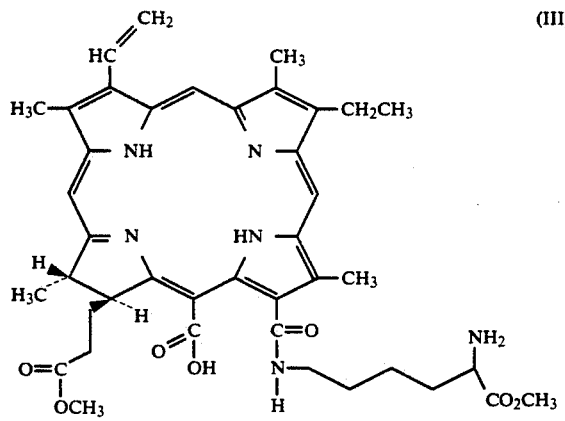

namely chlorin-p$_6$-6-N$^\epsilon$-lysylmethoxyamide-7-methyl ester, compound (III), which was obtained as a major product, and

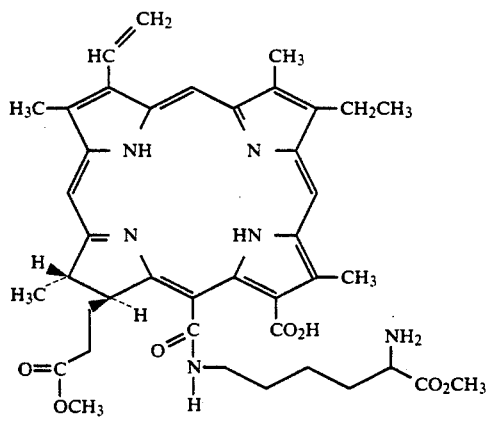

namely, chlorin-p$_6$-γ-N$^\epsilon$-lysylmethoxyamide-7-methyl ester, compound (IV).

Figure 4:
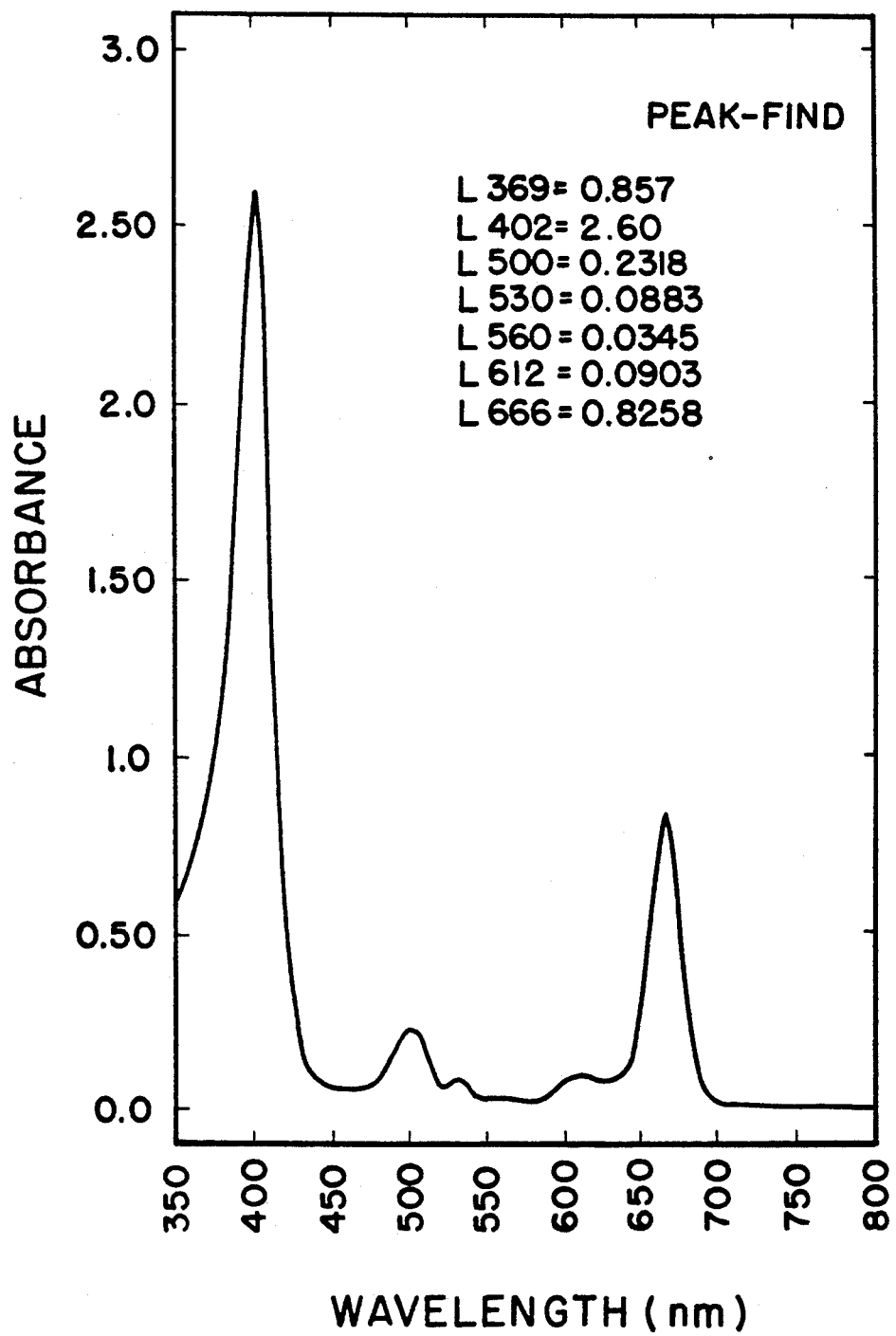
FIG. 4 is optical spectrum of chlorin-$p_6$ 6-$N^\epsilon$-lysylmethyoxyamide-7-methyl ester.
Figure 5:
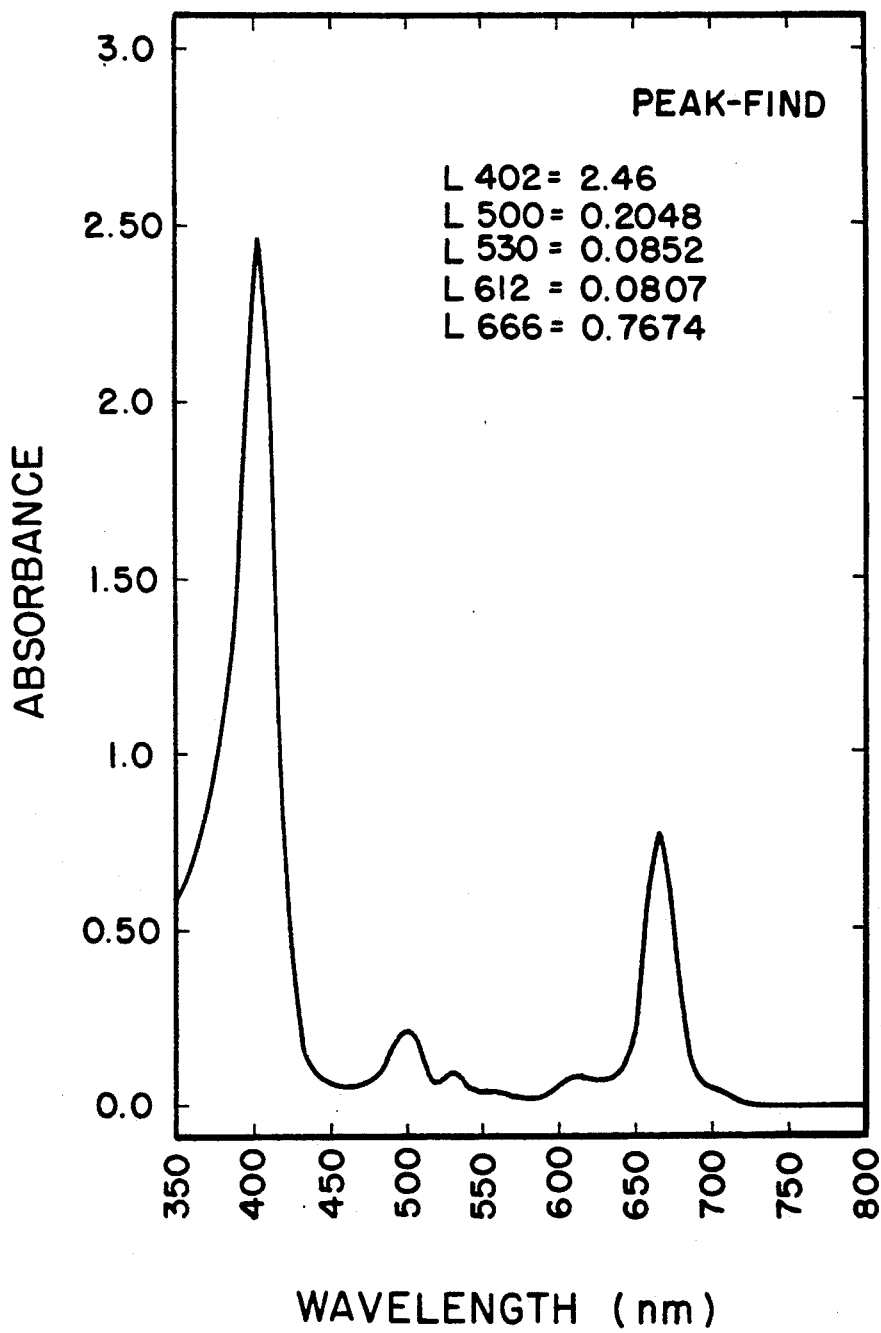
FIG. 5 is optical spectrum of chlorin-$p_6$ $\gamma$-$N^\epsilon$-lysylmethoxyamide-7-methyl ester.

Low resolution (Liquid SIMS) mass spectra of both products (III) and (IV) gave similar patterns and a protonated molecular ion at 739 (MH+). Elemental analysis of the major product C$_{41}$H$_{50}$N$_6$O$_7$H$_2$O found C: 65.48; H: 6.69; N: 10.77 against calculated C: 65.05; H: 6.93; N: 11.11. This confirmed that the product is a lysine adduct. The optical spectra of (III) and (IV) are essentially the same, as seen in FIG. 4 and FIG. 5, showing the major peak at 666 nm.

Esterification of (III ) and (IV) with diazomethane gave the corresponding dimethyl esters (V) and (VI).

Dimethyl ester (V) has formula

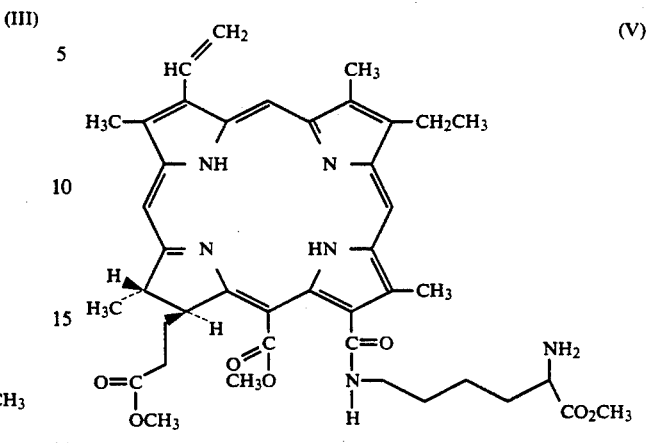

namely, chlorin-p$_6$-6-N$^\epsilon$-lysylmethoxyamide-γ,7-dimethyl ester.

Dimethyl ester (VI) has formula

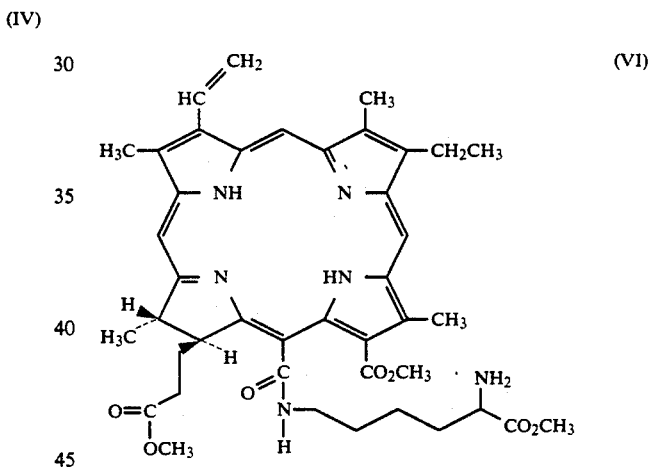

namely, chlorin-p$_6$-γ-N$^\epsilon$-lysylmethoxyamide-6,7-dimethyl ester.

High resolution electron impact (HREI) mass spectra gave a molecular ion of 752.3861 (Calculated 752.3897) for compound (V) and 752.3857 (Calculated 752.3897) for (VI). These indicate that both of them are chlorin-p$_6$ compounds with one lysine adduct.

Purpurin-18 Methyl Ester Anhydride Ring Opening by N-butylamine

Anhydride ring opening of purpurin-18 methyl ester (3) resulted in photosensitizer (VII) having a formula:

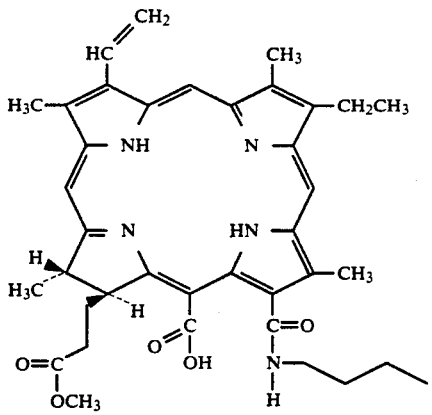

namely, chlorin-p6-6-N-butylamide-7-methyl ester, compound (VII).

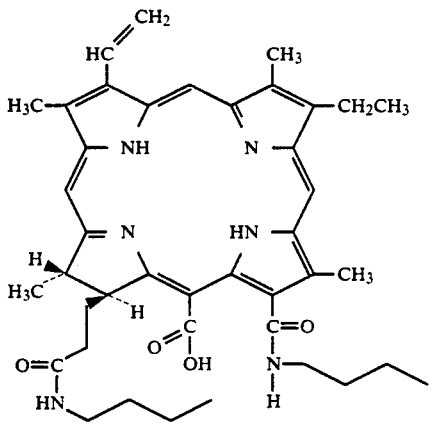

Compound (VIII) was prepared by adding an excess of n-butylamine to a solution of the purpurin-18 methyl ester in methylene chloride at room temperature. Soon after the addition, the color of the solution gradually changed from brown to green. Spectrophotometry showed the absorption at 700 nm to be decreasing, which indicated the consumption of purpurin-18 methyl ester (3) and formation of a new peak at 664 nm signifying a production of compound (VIII). One hour later no more starting material (3) was observed by spectrophotometry or TLC. After aqueous workup, the material was chromatographed on preparative silica gel TLC plates to give one green product in 90% yield with visible absorption at 664 nm corresponding to compound (VIII).

The $^1$NNMR of compound (VII) shows that the substituents remain unchanged in the 11–5 ppm region along with one additional broad triplet amide proton at 6.85 ppm which is in the range of a regular amide NH proton. Low resolution (Liquid SIMS) mass spectrometry gave a MH+ (652) peak and elemental analysis for $C_{38}H_{45}N_5O_5$ Found values: C: 68.04; H: 6.68; N: 9.93; which agreed with calculated C: 67.74; H: 6.58; N: 10.39), showing the product is a n-butylamine adduct. The compound (VII) however, appeared to be not very stable and readily decomposed back to purpurin-18 methyl ester (3) along with some very polar baseline material.

In order to eliminate the decomposition and fully characterize the product, compound (VII) was esterified with diazomethane to give the corresponding methyl ester (IX) of the formula

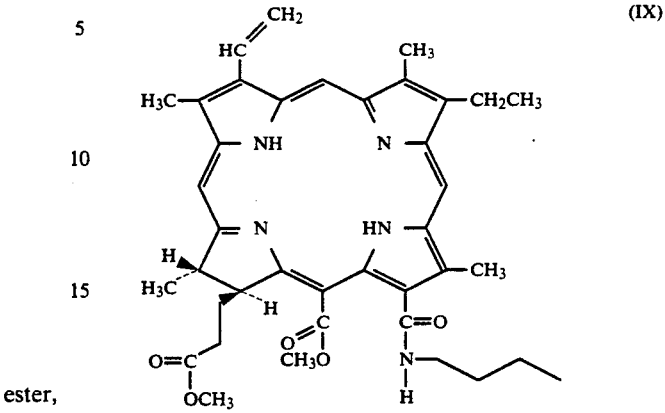

namely, chlorin-p6-6-N-butylamide-γ,7-dimethyl ester (VIII).

Compound III is stable at room temperature in the crystalline form and can be stored in methylene chloride solution in a refrigerator for up to six months.

Figure 3:
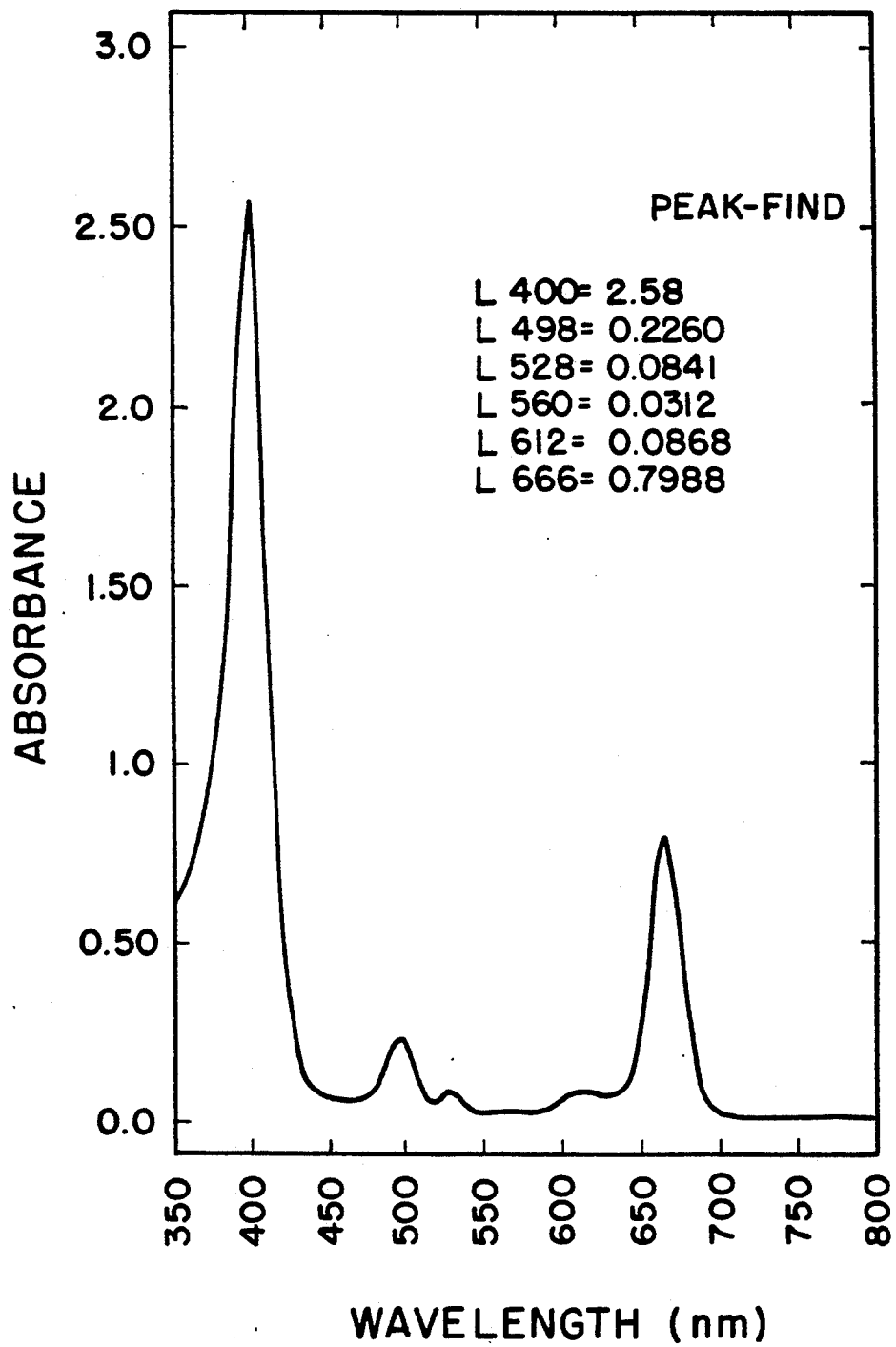
FIG. 3 is optical spectrum of chlorin-$p_6$-6-N-butylamide-$\gamma$,7-dimethyl ester.

The pattern of optical spectra of compound (III) is almost identical to spectra of compound (IX) as seen in FIG. 3. High resolution electron impact (HREI) mass spectrometry of compound (IX) gave a molecular ion at 665.3563 against calculated 665.3577; and elemental analysis for $C_{39}H_{47}N_5O_5$: Found C: 70.21; H: 7.20; N: 10.41; against that calculated C: 70.35; H, 7.12; N, 10.52.

During the above described synthesis of compound (VII), there was also produced a certain amount (~7%) of chlorin-p6 compound with two n-butyl amines attached which is seen as compound (VIII) above, namely, chlorin-p6-6,7-di-N-butylamide compound (IX) and after treatment with diazomethane, compound (X)

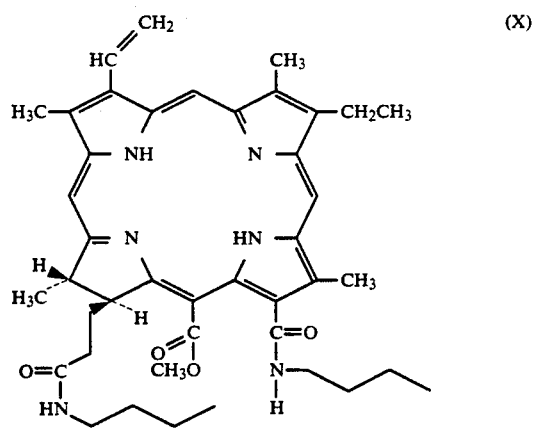

namely, chlorin-p6-6,7-di-N-butylamide-γ-methyl ester, compound (X).

Purpurin-18-Methyl Ester Anhydride Ring Opening by Ornithine

Ornithine which is an amino acid structurally similar to lysine but with one less side-chain methylene. Ornithine is commercially available as the hydrochloride salt. Similarly to lysine, ornithine opens the anhydride ring of purpurin-18 methyl ester to give compound (XI)

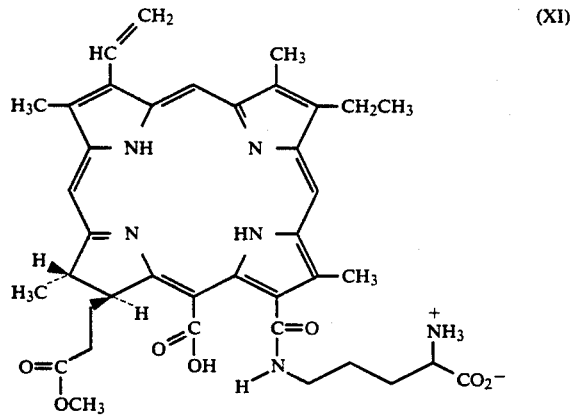

namely chlorin-$p_6$-6-N,$\gamma$-ornithylamide-7-methyl ester, compound (XI)

Esterification of compound (XI) yielded compound (XII) having formula

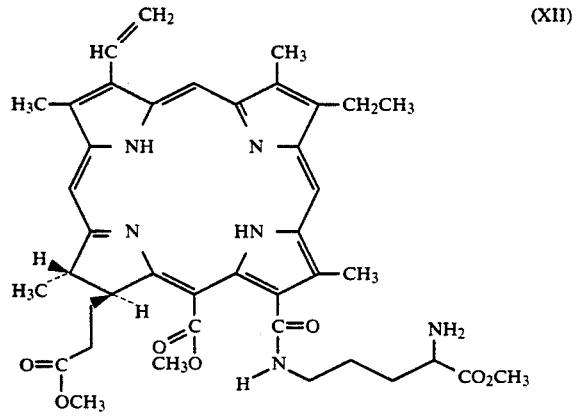

namely chlorin-$p_6$-6-N-ornithylmethoxyamide-$\gamma$,7-dimethyl ester, compound (XII).

Ornithine is poorly soluble in pyridine/water solutions. To neutralize ornithine HCl before reaction with purpurin-18 methyl ester (3), one equivalent of NaOH in aqueous solution was used. Water was then removed with a freeze dryer to obtain a white solid. Dried methanol was added into the ornithine-NaCl white solid. Sodium chloride and the ornithine-containing methanol solution were separated by decanting. The ornithine-containing methanol solution was subjected to rotovaporation to slowly remove the methanol. Ornithine solid was then precipitated out in concentrated methanol solution. During this process getting moisture into the methanol solution must be avoided or the precipitation of ornithine is inhibited and the process gives a gluey ornithine deposit. Ornithine was dissolved in a minimal amount of water then a maximal amount of pyridine was added and addition was stopped just before the ornithine-chlorin $p_6$ adduct precipitated out.

The $^1$HNMR spectrum of compound (XI) was similar to that of chlorin-$p_6$-6-N$^e$-lysylmethoxyamide-6,7-dimethyl ester (II).

Alternatively, purpurin-18 methyl ester (3) was dissolved in a minimal amount of pyridine and a maximal amount of water was then added, stopping just before purpurin-18 methyl ester precipitated out. The ornithine water/pyridine solution was added to the stirred purpurin-18 methyl ester (3) solution drop by drop. Addition was stopped the moment before either one of them began to precipitate out of solution. After 24 hours, spectrophotometry indicated most of purpurin-18 methyl ester (3) was consumed. The reaction solution was worked up, purified as the same way as that of chlorin-$p_6$-6-N$^\delta$-lysylamide-7-methyl ester (II) to give chlorin-$p_6$- 6-N$^\delta$-ornithylamide-7-methyl ester (XI).

The yield of chlorin-$p_6$ 6-N$^\delta$-ornithylmethoxyamide-$\gamma$,7-dimethyl ester (XII) is rather low. However, the optical spectrum of both compounds (XI) and (XII) possess the typical chlorin-$p_6$ pattern.

Physical properties such as melting point, UV absorption, high resolution mass spectra, and nuclear magnetic resonance for each compound were determined using methods known in the art.

Purpurin-18 Methyl Ester Anhydride Ring Opening by Methanol

The purpurin-18 methyl ester (3) anhydride ring can also be successfully opened with oxygen functionalities in alcohols or the nitrogen or oxygen functionalities in nucleotides.

Purpurin-18 methyl ester (3) was dissolved in methylene chloride followed by addition of a lysine/methanol solution. After one hour the color of the solution changed from brown to green which indicated the anhydride ring was open, and spectrophotometry and TLC showed complete consumption of purpurin-18 methyl ester (3). Upon aqueous work up and purification on preparative silica gel TLC plates a green compound was isolated in 80% yield. The $^1$HNMR spectrum did not show a triplet amide proton in the 6-7 ppm region and an unexpected three-hydrogen singlet appeared at 4.26 ppm accompanied by a small peak beside it, which was tentatively assigned as a structural isomer. The corresponding esterified compound with a visible absorption at 668 nm was obtained in 90% yield. The $^1$HNMR spectrum identified the compound as chlorin-$p_6$-trimethyl ester (XIII).

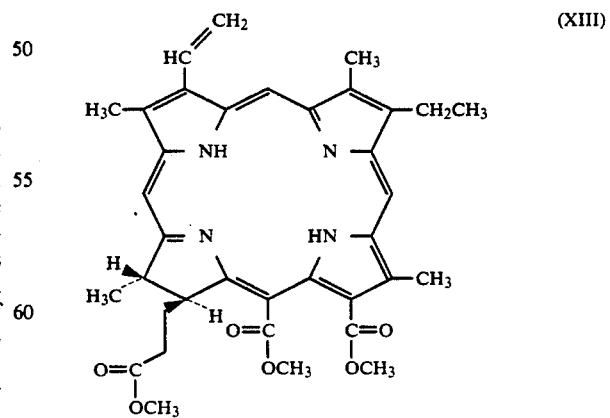

It seems that the methanol attacked the anhydride ring instead of lysine and produced (XIV) chlorin-$p_6$ dimethyl ester (XIV)

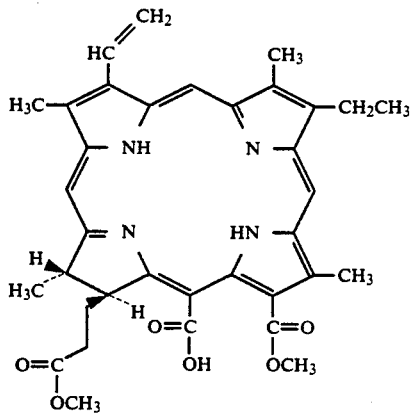 (XIV)

A solution of purpurin-18 methyl ester in methylene chloride with a maximal amount of methanol was then allowed to stir for 3 days, but no reaction occurred. This indicated that presence of lysine is essential in order for methanol to attack the anhydride ring, which means lysine acted as a weak base to promote the reaction.

Another reaction was carried out with purpurin-18 methyl ester in methylene chloride and methanol with a catalytic amount of triethylamine. The reaction was completed in one hour, and after treated with diazomethane gave chlorin-$p_6$ trimethyl ester (XIII) in 80% yield.

Photosensitizers of the current invention are potent antitumor agents. When selectively uptaken by tumors and subsequently irradiated, long term inhibition of tumor growth was achieved only at an energy density of 100 $J/cm^2$. When the rats received injection of the lysyl-chlorin (LCP) and were subsequently irradiated according to procedure described in Example 13, side effects of treatment were seen only in the irradiated area and consisted of coagulation necrosis of normal tissues in rats treated at 50 and 100 $J/cm^2$. Exposure of rats to fluorescent room light did not cause any macroscopically detectable skin damage. Data indicate that photodynamic destruction of subcutaneous 9L glioma tumors using LCP as a photosensitizer results in significant tumor growth inhibition.

The response obtained in rats following the irradiation of glioma was followed by observation of temperature changes. The results are illustrated in FIG. 1, which shows the light induced change in tumors when rats were injected with PBS or 2.5 mg/kg LCP and irradiated with 664-nm light. Five or six tumors were examined in each group, with the average temperature change plotted during and immediately following irradiation. The average starting temperature was 34.5° C. (range 33.0°–36.3° C.). A power density of 100 $mW/cm^2$ resulted in an average temperature rise of 6.6° C. in LCP-injected rats, compared to 3.1° C. in PBS injected rats. At a power density of 50 $mW/cm^2$, the mean temperature rise was only 3.8° C. in LCP-injected rats, while PBS injected rats had an average rise of 2.6° C. All subsequent experiments used a power density of 50 $mW/cm_2$ to minimize hyperthermic effects during tumor treatments.

Microscopic changes seen in tumors 24 hours after PDT consisted of congestion, thrombosis, and coagulation necrosis of tumor cells. The percent of tumor necrosis in each treatment group is shown in Table 1.

TABLE 1

| Percent Necrosis in 9L tumors 24 hours after PDT | |
|---|---|
| Treatment Parameters | % Necrosis |
| No injection, no light | 0.14 ± 0.24 |
| PBS, 100 $J/cm_2$ | 0.23 ± 0.63 |
| 2.5 mg/kg LCP, no light | 0.12 ± 0.16 |
| 2.5 mg/kg LCP, 25 $J/cm_2$ | 26.66 ± 25.85[a] |
| 2.5 mg/kg LCP, 50 $J/cm_2$ | 79.85 ± 9.14[a] |
| 2.5 mg/kg LCP, 100 J/cm 2 | 98.37 ± 0.84[a] |

[a]significantly different from no injection, no light group: p <0.02.

Rats were killed 24 hours after PDT treatment. Tumors were evaluated microscopically after immersion fixation in 10% neutral buffered formalin, routine processing, sectioning, and then staining with hematoxylin and eosin (H&E). Means±SD expressed in % necrosis are shown. N=5/group.

Less than 1% tumor necrosis was seen in tumors from the untreated group, and there was no significant difference in tumor necrosis between the untreated group, the rats injected with photosensitizer only, or the rats irradiated but not injected with photosensitizer. The percent tumor necrosis in rats injected with LCP and then irradiated increased with higher energy densities. Treatment with 100 $J/cm^2$ resulted in a mean of 98.4% tumor necrosis, with viable tumor cells observed only at the deep border of the tumor in the 100 $J/cm^2$ treatment group. All groups injected with LCP and irradiated had significantly greater tumor necrosis compared to the untreated group (P<0.02). The extent of tumor necrosis in the group treated at 25 $J/cm^2$ was quite variable between individual animals, while in other groups results were more consistent. Additional microscopic changes in adjacent fat, muscle, and overlying skin were congestion, edema, and necrosis. The severity of changes in normal tissues paralleled that seen in tumors, with more normal tissue damage seen at higher energy doses. Minimal normal tissue damage was seen at 25 $J/cm^2$.

Results from tumor regrowth studies are shown in Table 2. Five rats were examined in each group.

TABLE 2

| Tumor Regrowth following PDT | |
|---|---|
| Treatment Parameters | Days to Six Fold Increase in Tumor Volume (means ± SD) |
| No injection, no light | 12.4 ± 2.61 |
| PBS, 100 $J/cm^2$ | 13.6 ± 4.34 |
| 2.5 mg/kg LCP, no light | 11.2 ± 1.01 |
| 2.5 mg/kg LCP, 25 $J/cm^2$ | 11.2 ± 1.79 |
| 2.5 mg/kg LCP, 50 $J/cm^2$ | 14.4 ± 3.58 |
| 2.5 mg/kg LCP, 100 J/cm 2 | 47.4 ± 10.43[a] |

[a]significantly different from no injection, no light group: P <0.02.

Rats were given LCP i.v. followed 4 hours later by irradiation with 664-nm light. Means±SD expressed in days until a six fold increase in tumor volume was detected are shown. N=5 rats/group.

Tumor growth was similar in all groups except those given 2.5 mg/kg LCP and a light dose of 100 $J/cm^2$. This treatment significantly lengthened the mean of the days to a sixfold tumor volume increase from 12.4 days in untreated controls to 47.6 days (P<0.02). Although there was a slight increase in mean tumor regrowth time of rats treated with LCP and irradiated with 50 $J/cm^2$ compared to controls, the differences were not statistically significant.

Table 3 shows the skin responses observed in the irradiated filed.

TABLE 3

Skin Scores from Rats Treated with PDT

| Treatment Parameters | Skin Score in Irradiated Field (means ± SD) |
|---|---|
| No injection, no light | 0.00 ± 0.00 |
| PBS, 100 J/cm$^2$ | 0.00 ± 0.00 |
| 2.5 mg/kg LCP, no light | 0.00 ± 0.00 |
| 2.5 mg/kg LCP, 25 J/cm$^2$ | 1.20 ± 1.64 |
| 2.5 mg/kg LCP, 50 J/cm$^2$ | 5.00 ± 0.00 |
| 2.5 mg/kg LCP, 100 J/cm$_2$ | 6.00 ± 0.00 |

Rats were given LCP i.v. followed 4 hours later by irradiation with 664-nm light. Mean skin score±SD is shown. N=5 rats/group.

Skin responses were very uniform within groups, with the exception of the group treated at 25 J/cm$^2$ in which scores ranged from 0 to 3. There was no skin damage on the ears or feet in any group, despite exposure to fluorescent room light throughout the duration of the experiments. Within the irradiated field, responses were only seen in animals receiving photosensitizer prior to irradiation. The amount of skin damage in the irradiated field was related to the energy dose, with minimal skin damage at 25 J/cm$^2$ and a large area of necrosis of skin overlying the tumor at 100 J/cm$^2$.

Data summarized in Table 2-4 demonstrate that photodynamic therapy of subcutaneous 9L glioma tumors using LCP as the photosensitizer results in significant tumor destruction and growth inhibition. Skin photosensitization was not seen except in tissues which received direct irradiation. No systemic toxic effects were noted clinically or pathologically at the dose of photosensitizer used (2.5 mg/kg).

Microscopic changes in tumors and surrounding tissues examined 24 hours following PDT were similar to those described using other photosensitizers, namely localized congestion, edema, and coagulation necrosis. Necrosis was minimal in control animals, and neither drug alone nor light alone appeared to have any effect on the microscopic appearance or growth of the tumors. The percent necrosis in PDT-treated tumors increased as the energy density was increased, indicating more activation of the photosensitizer.

Microscopic examination of several animals 7-10 days after LCP injection and irradiation at 100 J/cm$^2$ showed there was 100% tumor necrosis, and therefore, complete tumor cures would be expected.

Skin responses were uniform within groups and skin damage was not seen in any rats except those injected with LCP and then irradiated with 664-nm light. Fluorescent room light did not appear to cause any cutaneous effects at the photosensitizer dose of 2.5 mg/kg. Normal tissue damage (coagulation necrosis with subsequent scarring) was seen in tissues which were directly irradiated, including skin, fat, and muscle adjacent to the tumor, and in the immediately underlying colon and kidney. Normal tissue damage was mild at a fluence of 50 mW/cm$^2$ and more severe at 100 mW/cm$^2$. Rats repaired such damage, as indicated by ability of several to survive in good healthy for over 50 days after irradiation in the group receiving the highest energy dose.

These studies indicate that the current sensitizers are effective for use in PDT. While PDT using LCP does not cause cutaneous photosensitization in nonirradiated skin, directly irradiated tissues including skin were damaged during treatment.

UTILITY

The novel photosensitizers of the current invention are useful for a photodynamic diagnosis and treatment of neoplasia. New photosensitive compounds have selective tumoricidal uptake and can be irradiated by long wave light without many of the serious side effects observed with conventional therapy, such as radiotherapy or chemotherapy of tumors.

Photosensitizers of the current invention selectively destroy tumor tissue without disruption of normal tissue function. Photosensitizers are selectively and quantitatively uptaken and retained by the tumor tissue and subsequently photosensitized by light at wavelength specific to each photosensitizer in the presence of oxygen.

While the exact mechanism of the retention and photosensitization is not known in case of these new photosensitizers, they are selectively taken up by tumor cells and retained or trapped within the tumor cell. Their photosensitization is based on a photosensitized oxidation process probably involving singlet oxygen which causes cell toxicity in photodynamic therapy.

In the photosensitized oxidation, upon activation with light, an electron of the chlorophyll derivative nucleus is excited from the singlet ground-state to a singlet excited state. The electron then can either return to the singlet ground-state with the emission of light (fluorescence; for use in tumor detection), or it can change its spin, as a therapeutic useful photosensitizer does, via intersystem crossing to the triplet state which has a longer lifetime. The decay of the triplet to the singlet ground state is a slow process because the transition is forbidden according to the spectroscopic selection rules.

The triplet sensitizer interacts with other molecules by two principal modes, so-called Type I and Type II reactions as seen in Reaction Scheme II.

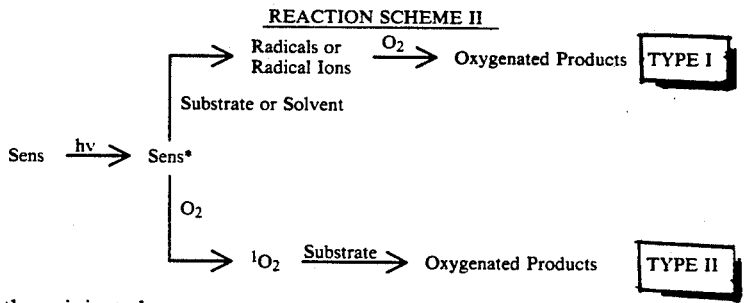

REACTION SCHEME II

High oxygen concentrations favor the Type II reaction and high substrate concentrations promote the Type I. The Type I reaction results in either hydrogen atom or electron transfer, yielding radicals or radical ions. Transfer can occur in either direction, but most commonly, the excited sensitizer acts as an oxidant. The Type II reaction leads mainly to the formation of singlet oxygen, the putative cytotoxic agent. Singlet oxygen is a short-lived (approx. 1-10 msec) excited state of molecular oxygen which is a strong oxidizing agent. In some cases, electron transfer from sensitizer to oxygen can occur, giving oxidized sensitizer and superoxide ion.

In practice, photosensitizers of this invention are purified and prepared as a liquid or powder either by freeze drying, lyophilization, or by other procedures customarily used in the pharmaceutical industry. Typically, the dry powder is dissolved in sterile saline, phosphate buffer, or any other solvent suitable for human administration. If necessary, pH is adjusted to 7.3-7.4; however, for routine use, the solvent for solution preparation are already pH adjusted and are supplied together with the photosensitizer powder for immediate use. Before use, the powder and the solvent are optimally stored in darkness in a cool place, preferably at 4° C. For use, the fresh solution is prepared. However, preprepared solution is storagable at 4° C. about 4-48 hours, preferably for no more than 24 hours.

Before use, each individual photosensitizer has predetermined an irradiation long wavelength absorption maxima peak. This wavelength is then used for irradiation of the treated tumor or for the tumor diagnosis.

Patients which are undergoing a tumor therapy or being diagnosed for the presence of the tumor are injected with a photosensitizer in a solution, as described above, in amount from 0.01-100 mg/kg, preferably around 1-10 mg/kg of the photosensitizer. The amount of the photosensitizer depends on its toxicity, tumor specificity and reactivity. These properties are unique to each individual compound and they vary from compound to compound.

After 1-48 hours, preferably between 4-24 hours following the i.v. injection of the photosensitizer to a patient, the individual is irradiated with the wavelength showing the highest absorption peak for the particular photosensitizer. The irradiation is applied from 1 minute to several hours, preferably around 30-60 minutes at energy doses preferably between 100 and 200 J/cm$^2$. The energy may be lower or higher depending on tolerance of the individual, on the tumor, on the size and the location of the tumor. Irradiation of the tumor usually utilizes a power density of around 25-100, preferably 50 mW/cm$^2$ with total laser energy densities between 25-100 J/cm$^2$. The light is preferably delivered directly to a tumorous tissue mass with fiber optics from a laser.

In general, for diagnostic purposes the energy, power, density, time and dose of the photosensitizer are lower than for the therapeutic purpose. In the diagnostic use of this invention, the compound is administered only once and irradiated also only one time. For therapeutic purposes, the therapeutic regimen depends on the size, location, and type of tumor and may be one time treatment or multiple repeated treatments on daily or monthly basis as become necessary. All these and other modes of administration and use are intended to be within scope of this invention.

The following examples are intended to illustrate the current invention. They are not to be interpreted in any way limiting the scope of the invention.

EXAMPLE 1

Preparation of Methyl Pheophorbide-a

This example illustrates preparation of a precursor methyl pheophorbide-a (2) from commercial algae.

Commercial algae, *Spirulina maxima* (1 Kg), was wetted with acetone (500 mL) to make a slurry and liquid nitrogen (4 L) was carefully added to the slurry in a large Dewar. After treating the wetted cells with nitrogen for 30 min these frozen cells were transferred to a 5 L round bottom flask and refluxed for 3 to 4 hours before filtering off the algal cells. The green solid was transferred back to the round bottom flask with additional acetone (4 L), refluxed again for 3 hours and the cells were again filtered off. This process was repeated one more time if necessary.

The combined chlorophyll-a/acetone solution was evaporated (eventually with a vacuum oil pump) until all acetone was removed, leaving a black oily residue. The black residue was dissolved in 5% sulfuric acid/methanol (30 mL conc. H$_2$SO$_4$+570 mL MeOH) and stirred in the dark under nitrogen for 20 h. After this time methylene chloride (600 mL) was added and the solution was poured into water (600 mL). The organic layer was then separated from the aqueous layer which was further extracted with methylene chloride until the aqueous layer was no longer green. The combined organic layer was then carefully poured into aqueous sodium bicarbonate. After separating the organic layer it was washed with water several times until the aqueous layer was no longer basic. It was then dried, and evaporated to dryness. The product was purified on Grade V neutral alumina, eluting first with 90/10 of toluene/methylene chloride to remove a fast-running yellow band, and then with 80/20 of toluene/methylene chloride to remove the major product. After evaporating the solvents the residue was crystallized from methylene chloride/methanol or methylene chloride/n-hexane to yield 1.3 g of methyl pheophorbide-a (2).

mp 223°-225° C. (lit. 228° C.);

UV $\lambda_{max}$ (CH$_2$Cl$_2$) 668 nm ($\epsilon$ 4.46×10$^4$), 610 (8.62×10$^3$), 538 (9.71×10$^3$), 506 (1.08×10$^4$), 412 (1.06×10$^5$).

$^1$HNMR (300 MHz, CDCl$_3$) $\delta$, ppm, 9.50 (s, $\beta$-meso H), 9.35 (s, $\alpha$-meso H), 8.56 (s, $\delta$-meso H), 7.97 (X of ABX, 2a-H), 6.29, 6.16 (AB of ABX, 2b and 2b'-H), 6.25 (s, 10-H), 4.46 (q, J=7.3 Hz, 8-H), 4.20 (d, J=9 Hz, 7-H), 3.88 (s, 10-CO$_2$Me), 3.66 (q, J=7.6 Hz, 4a-CH$_2$), 3.68 (s, 7d-OMe), 3.57 (s, 5-Me), 3.40 (s, 1-Me), 3.21 (s, 3-Me), 2.64 (m,7a-H), 2.52 (m,7b-H), 2.32 (m,7a'-H), 2.23 (m,7b'-H), 1.81 (d, J=7.3 Hz, 8-Me), 1.69 (t, J=7.6 Hz, 4b-Me), 0.53, −1.63 (each br s, NH).

EXAMPLE 2

Preparation of Purpurin-18 Methyl Ester

This example illustrates preparation of purpurin-18 methyl ester (3).

Methyl pheophorbide-a (2) prepared in Example 1 (300 mg, 0.49 mmole) was dissolved in warm pyridine (5 mL) and the solution was diluted with ether (500 mL). The solution was stirred with a stream of air passing through it, and a solution of potassium hydroxide (4 g) in n-propanol (10 mL) was added. The bright green mixture containing precipitated potassium hydroxide was stirred and aerated for 30 min and then extracted with water until the ethereal layer was no longer green. The ethereal solution was discarded, the aqueous extracts were combined and adjusted to pH~4 with concentrated sulfuric acid (~4 mL). Then the mixture was extracted with methylene chloride until the aqueous layer was no longer green-brown. The combined methylene chloride extract containing so-called "unstable chlorin" was subjected to repeated evaporation and redissolution in distilled THF until no further increase in visible absorption at 700 nm was observed. The product was esterified with ethereal diazomethane, then washed with water, dried and evaporated to dryness. The product was purified on preparative TLC plates, eluting with 2% methanol in methylene chloride to give a purple-brown band. After evaporating the solvents, the residue was crystallized from methylene chloride/methanol to yield 143 mg (50%) of purpurin-18 methyl ester (3).

UV $\lambda_{max}$ ($CH_2Cl_2$) 698 nm ($\epsilon$ 4.98×10$^4$), 642 (9.85×10$^3$), 592 (3.16×10$^3$), 546 (2.46×10$^4$), 508 (7.52×10$^3$), 478 (5.13×10$^3$), 410 (1.23×10$^5$);

$^1$HNMR (300 MHz, CDCl$_3$) $\delta$, ppm, 9.55 (s, $\beta$-meso H), 9.35 (s, $\alpha$-meso H), 8.57 (s, $\delta$-meso H), 7.88 (dd, J=18, 11.7 Hz, 2a-H), 6.29 (d, J=18 Hz, 2b-H), 6.18 (d, J=11.7 Hz, 2b'-H), 5.17 (d, J=9.3 Hz, 7-H), 4.38 (q, J=7.2 Hz, 8-H), 3.76 (s, 3H), 3.62 (q, J=7.5 Hz, 4a-CH$_2$), 3.60 (s, 3H), 3.34 (s, 3H), 3.12 (s, 3H), 2.73 (m, 7b-H), 2.47 (m, 7b'-H), 2.43 (m, 7a-H), 1.99 (m, 7a'-H), 1.74 (d, J=7.2 Hz, 8-Me), 1.65 (t, J=7.5 Hz, 4b-Me), 0.21, −0.09 (each br s, NH);

HR mass spectrum: $C_{34}H_{34}N_4O_5$ requires 578.2529; found 578.2509.

EXAMPLE 3

Preparation of Chlorin-p$_6$ Trimethyl Ester and Chlorin-p$_6$ Dimethyl Ester This example illustrates preparation of chlorin-p$_6$ trimethyl ester (XIII) and dimethyl ester (XIV) by three different procedures A, B, and C.

(A) Purpurin-18 methyl ester (30 mg, 0.052 mmole) was dissolved in methylene chloride (20 mL), to which was added lysine (600 mg, 4 mmole) dissolved in methanol (20 mL). This mixture was stirred at room temperature in the dark under nitrogen for 2 hours; checking with spectrophotometry and TLC at this time showed no remaining starting material.

The solvents were evaporated at room temperature, redissolved in methylene chloride, washed with water (4×50 mL), dried, and evaporated to dryness. The material was purified by preparative TLC, eluting with 92/8 methylene chloride/methanol to give chlorin-p$_6$-6,7-dimethyl ester (28.5 mg, 90%). The chlorin-p$_6$-6,7-dimethyl ester was dissolved in methylene chloride and treated with excess etheral diazomethane, then washed with water, dried and evaporated to dryness. The product was purified on preparative TLC, eluting with 98/2 methylene chloride/methanol. After evaporating the solvents the residue was crystallized from methylene chloride/n-hexane to yield 26 mg (80%) of chlorin-p$_6$ trimethyl ester.

(B) Purpurin-18 methyl ester (30 mg, 0.052 mmole) was dissolved in a solution of methylene chloride and methanol (1:1, 40 mL), to which was added 3 drops of triethylamine. The mixture was stirred at room temperature in the dark under nitrogen for 2 hours and checked with spectrophotometry and TLC to show that no remaining starting material remained. The solvents were evaporated at room temperature and eventually with an oil pump to remove the residual traces of triethylamine. The material was purified as described in method A to yield 28 mg (93%) of chlorin-p$_6$ 6,7-dimethyl ester and 26 mg (86%) of chlorin-p$_6$ trimethyl ester.

(C) Purpurin-18 methyl ester (30 mg, 0.052 mmole) was dissolved in 0.1N sodium hydroxide in 50% methanol (20 mL). This mixture was stirred at room temperature in the dark under nitrogen for 1 hour, whereupon spectrophotometry showed no remaining starting material. The aqueous solution was adjusted to pH~7 with dilute hydrochloric acid and extracted with methylene chloride until no longer green. The combined organic layer was evaporated at room temperature and the material was purified by preparative TLC, and eluted with 85/15 methylene chloride/methanol to yield 18.6 mg (60%) of chlorin-p$_6$ 6-methyl ester.

The above chlorin-p$_6$ 6-methyl ester was dissolved in a small amount of methanol and then diluted with methylene chloride. The solution was treated with excess etheral diazomethane immediately, then washed with water, dried and evaporated to dryness. The product was purified as described in method A to yield 16.2 mg (50%) of chlorin-p$_6$ trimethyl ester (XIII).

Physical data -Chlorin-p$_6$ 6,7-Dimethyl Ester (XIV)

$^1$HNMR (300 MHz, CDCl$_3$) $\delta$, ppm, 9.75 (s, $\beta$-meso H), 9.51 (s, $\alpha$-meso H), 8.69 (s, $\delta$-meso H), 8.03 (dd, J=17.8, 11.5 Hz, 2a-H), 6.38 (dd, J=17.8, 1.0 Hz, 2b-H), 6.18 (dd, J=11.5, 1.0 Hz, 2b'-H), 5.33 (d, J=11.8 Hz, 7-H), 4.46 (q, J=7.2 Hz, 8-H), 4.26 (s, 3H), 3.79 (q, J=7.5 Hz, 4a-CH$_2$), 3.71 (s, 3H), 3.53 (s, 3H), 3.46 (s, 3H), 3.30 (s, 3H), 2.43-2.20, 2.04-1.96 (m, 7a & 7b-CH$_2$CH$_2$), 1.87 (d, J=7.2 Hz, 8-Me), 1.73 (t, J=7.5 Hz, 4b-Me), −0.63, −0.77 (each br s, NH).

Physical Data Chlorin-p$_6$ 6-Methyl Ester $^1$HNMR (300 MHz, CDCl$_3$) $\delta$, ppm, 9.71 (s, $\beta$-meso H), 9.50 (s, $\alpha$-meso H), 8.72 (s, $\delta$-meso H), 7.95 (dd, J=17.7, 11.5 Hz, 2a-H), 6.33 (d, J=17.7 Hz, 2b-H), 6.14 (d, J=11.5 Hz, 2b'-H), 5.40 (d, J=12 Hz, 7-H), 4.48 (q, J=7.2 Hz, 8-H), 4.24 (s, 3H), 3.72 (q, J=7.5 Hz, 4a-CH$_2$), 3.63 (s, 3H), 3.42 (s, 3H), 3.25 (s, 3H), 2.67-2.60, 2.34-2.00 (m, 7a & 7b-CH$_2$CH$_2$), 1.92 (d, J=7.2 Hz, 8-Me), 1.71 (t, J=7.5 Hz, 4b-Me), −0.89 (each br s, NH).

Physical Data Chlorin-p$_6$ Trimethyl Ester (XIII)

mp 235°-236° C. (lit. mp 236° C.);

UV $\lambda_{max}$ ($CH_2Cl_2$) 668 nm ($\epsilon$ 4.09×10$^4$), 614 (4.85×10$^3$), 532 (5.49×10$^3$), 498 (9.92×10$^3$), 402 (1.37×10$^5$);

$^1$HNMR (300 MHz, CDCl$_3$) $\delta$, ppm, 9.70 (s, $\beta$-meso H), 9.49 (s, $\alpha$-meso H), 8.66 (s, $\delta$-meso H), 7.98 (dd, J=18, 11.7 Hz, 2a-H), 6.31 (dd, J=18, 0.9 Hz, 2b-H), 6.14 (dd, J=11.7, 0.9 Hz, 2b'-H), 5.17 (d, J=12 Hz, 7-H), 4.41 (q, J=7.2 Hz, 8-H), 4.25 (s, 3H), 4.19 (s, 3H), 3.74 (q, J=7.5 Hz, 4a-CH$_2$), 3.67 (s, 3H), 3.54 (s, 3H), 3.41 (s, 3H), 3.24 (s, 3H), 2.39 (m, 7b-H), 2.22 (m, 7a-H), 2.07 (m, 7b'-H), 1.91 (m, 7a'-H), 1.87 (d, J=7.2 Hz, 8-Me), 1.71 (t, J=7.5 Hz, 4b-Me), −0.84, −1.02 (each br s, NH);

HR mass spectrum: $C_{36}H_{40}N_4O_6$ requires 624.2947; found 624.2926.

EXAMPLE 4

Preparation of Chlorin-p$_6$-6-N-Butylamide-7-Methyl Ester

This example illustrates preparation of chlorin-p$_6$-6-N-butylamide-7-methyl ester (VII) by opening anhydride ring of purpurin-18-methyl ester with N-butylamine.

A solution of purpurin-18 methyl ester (30 mg, 0.052 mmole) in methylene chloride (20 mL) was cooled to 0° C. and n-butylamine (0.5 mL, 5 mmole) was added. This mixture was stirred at room temperature in the dark under nitrogen for 2 hours, whereupon spectrophotometry and TLC showed no remaining starting material. Then the reaction mixture was diluted with methylene chloride (100 mL), washed with water (2×50 mL), dried, and evaporated to dryness to remove the residual trace of n-butylamine. The product was purified by preparative TLC, eluting with 88/12 methylene chloride/methanol. After evaporating the solvents, the residue was crystallized from methylene chloride/n-hexane to yield 30 mg (90%) of chlorin-p$_6$ 6-N-butylamide-7-methyl ester (VII).

mp>300° C.;

UV $\lambda_{max}$ (CH$_2$Cl$_2$) 664 nm ($\epsilon$ 4.56×10$^4$), 608 (1.08×10$^4$), 532 (1.13×10$^4$), 500 (1.90×10$^4$), 404 (1.37×10$^5$).

$^1$HNMR (300 MHz, CDCl$_3$) $\delta$, ppm, 9.65 (s, $\beta$-meso H), 9.60 (s, $\alpha$-meso H), 8.60 (s, $\delta$-meso H), 8.09 (br dd, J=18, 11 Hz, 2a-H), 6.33 (d, J=18 Hz, 2b-H), 6.12 (d J=11 Hz, 2b'-H), 6.85 (br t, 6-n-butylamine-CONH), 4.88 (br d, 7-H), 3.98 (br q, 8-H), 3.77 (m, 6-n-butylamine-a-CH$_2$), 3.63 (br q, 4a-CH$_2$), 3.40 (br s, 2×3H), 3.33 (br s, 2×3H), 2.50-2.00 (m, 7a & 7b-CH$_2$CH$_2$), 1.75 (br d, 8-Me), 1.43 (br t, 4b-Me), 126–1.00 (br m, 6-n-butylamine-b & c-CH$_2$CH$_2$), 0.54 (br t, 6-n-butylamine-d-CH$_3$), −1.72, −2.06 (each br s, NH);

LR mass spectrum: 652 (MH+).

Anal. Calcd. for C$_{38}$H$_{45}$N$_5$O$_5$: C, 67.74; H, 6.58; N, 10.39. Found: C, 68.04; H, 6.68; N, 9.93.

EXAMPLE 5

Preparation of Chlorin-p$_6$-6,7-Di-N-butylamide

This example illustrates preparation of chlorin-p$_6$ 6,7-di-n-butylamide (VIII).

Purpurin-18 methyl ester (30 mg, 0.052 mmole) was dissolved in n-butylamine (20 mL). This mixture was stirred at room temperature in the dark under nitrogen for 30 min, whereupon spectrophotometry showed no remaining starting material. Then the reaction mixture was diluted with methylene chloride (200 mL), washed with water (2×50 mL), dried, and evaporated to dryness to remove the trace of n-butylamine. The crude product was purified by preparative TLC, eluting with 88/12 methylene chloride/methanol to give two major products in ratio of 7 to 3. The faster-running green band was the chlorin-p$_6$ 6-N-butylamide-7-methyl ester (VII). The slower-running green band was the chlorin-p$_6$ 6,7-di-N-butylamide (VIII). Both green compounds were crystallized from methylene chloride/n-hexane to give (21 mg, 63%) of compound (VII) and (8 mg, 22%), of compound (VIII) respectively.

mp>300° C.;

UV $\lambda_{max}$ (CH$_2$Cl$_2$) 664 nm ($\epsilon$ 3.55×10$^4$), 610 (4.03×10$^3$), 528 (3.48×10$^3$), 500 (1.08×10$^4$), 404 (1.27×10$^5$);

LR mass spectrum: 693 (MH+).

EXAMPLE 6

Preparation of Chlorin-p$_6$-6-N-butylamide-$\gamma$, 7-dimethyl Ester

This example illustrates preparation of chlorin-p$_6$-6-n-butylamide-$\gamma$,7-dimethyl ester (IX).

The crude product of chlorin-p$_6$ 6-N-butylamide-7-methyl ester (VII) (30 mg, 0.046 mmole) was dissolved in methylene chloride and treated with excess ethereal diazomethane, then washed with water, dried and evaporated to dryness. The product was purified by preparative TLC and eluted with 96/4 methylene chloride/methanol. After evaporating the solvents the residue was crystallized from methylene chloride/n-hexane to yield 27.5 mg (90%) of chlorin-p$_6$ 6-N-butylamide-$\gamma$,7-dimethyl ester (IX).

mp 229°–231° C.;

UV $\lambda_{max}$ (CH$_2$Cl$_2$) 666 nm ($\epsilon$ 4.34×10$^4$), 612 (3.47×10$^3$), 562 (3.90×10$^2$), 528 (3.30×10$^3$), 498 (1.12×10$^4$), 400 (1.50×10$^5$);

$^1$HNMR (300 MHz, CDCl$_3$) $\delta$, ppm, 9.72 (s, $\beta$-meso H), 9.62 (s, $\alpha$-meso H), 8.77 (s, $\delta$-meso H), 8.04 (dd, J=17.7, 11.4 Hz, 2a-H), 6.34 (dd, J=17.7, 1.5 Hz, 2b-H), 6.21 (t, J=5.7 Hz, 6-n-butylamine-CONH), 6.15 (dd, J=11.4, 1.5 Hz, 2b'-H), 5.04 (d, J=8.1 Hz, 7-H), 4.44 (q, J=7.2 Hz, 8-H), 4.22 (s, 3H), 3.87 (m, 6-n-butylamine-a-H), 3.75 (q, J=7.5 Hz, 4a-CH$_2$), 3.70 (m, 6-n-butylamine-a'-H), 3.62 (s, 3H), 3.46 (s, 3H), 3.45 (s, 3H), 3.28 (s, 3H), 2.40 (m, 7b-H), 2.29 (m, 7a-H), 2.03 (m, 7b'-H), 1.98 (m, 7a'-H), 1.84 (d, J=7.2 Hz, 8-Me), 1.77 (m, 6-n-butylamine-b-CH$_2$), 1.70 (t, J=7.5 Hz, 4b-Me), 1.55 (m, 6-n-butylamine-c-CH$_2$), 1.04 (t, J=7.8 Hz, 6-n-butylamine-d-Me), −1.32, −1.55 (each br s, NH);

HR mass spectrum: C$_{39}$H$_{47}$N$_5$O$_5$ requires 665.3577; found 665.3564;

Anal. Calcd. for C$_{39}$H$_{47}$N$_5$O$_5$: C, 70.35; H, 7.12; N, 10.52. Found: C, 70.21; H, 7.20; N, 10.41

EXAMPLE 7

Preparation of Chlorin-p$_6$,6,7-Di-N-Butylamide-$\gamma$-Methyl Ester

This example illustrates preparation of chlorin-p$_6$-6,7-di-n-butylamide-$\gamma$-methyl ester (X).

The chlorin-p$_6$-6,7-di-N-butylamide (VIII) (6 mg, 0.0087 mmole) was esterified with ethereal diazomethane, then washed with water, dried and evaporated to dryness. The product was purified by preparative TLC, eluting with 95/4 methylene chloride/methanol. After evaporating the solvents the residue was crystallized from methylene chloride/n-hexane to yield 3 mg (50%) of chlorin-p$_6$-6,7-di-N-butylamide-$\gamma$-methyl ester (X).

mp 114°–115° C.;

UV $\lambda_{max}$ (CH$_2$Cl$_2$) 666 nm ($\epsilon$ 4.22×10$^4$), 614 (4.57×10$^3$), 564 (1.53×10$_3$), 530 (4.45×10$^3$), 498 (1.21×10$^4$), 400 (1.44×10$^5$);

$^1$HNMR (300 MHz, CDCl$_3$) $\delta$, ppm, 9.73 (s, $\beta$-meso H), 9.61 (s, $\alpha$-meso H), 8.76 (s, $\delta$-meso H), 8.04 (dd, J=17.9, 11.6 Hz, 2a-H), 6.39 (t, J=5.7 Hz, 6-n-butylamine-CONH), 6.34 (dd, J=17.9, 1.0 Hz, 2b-H), 6.15 (dd, J=11.6, 1.0 Hz, 2b'-H), 5.03 (dd, J=7.2, 2.4 Hz, 7-H), 4.65 (t, J=5.1 Hz, 7c-n-butylamine-CONH), 4.46 (q, J=7.2 Hz, 8-H), 4.20 (s, 3H), 3.86 (m, 6-n-butylamine-a-H), 3.76 (q, J=7.5 Hz, 4a-CH$_2$), 3.69 (m, 6-n-butylamine-a'-H), 3.62 (s, 3H), 3.46 (s, 3H), 3.29 (s, 3H), 2.75 (m, 7c-n-butylamine-a-H), 2.49 (m, 7c-n-butylamine-a'-H), 2.36 (m, 7a-H), 2.24 (m, 7a'-H), 1.97 (m, 6-n-butylamine-b-H), 1.83 (d, J=7.2 Hz, 8-Me), 1.77 (m, 6-n-butylamine-b'-H), 1.71 (t, J=7.5 Hz, 4b-Me), 1.56 (m, 7b-CH$_2$), 1.45 (m, 6-n-butylamine-c-CH$_2$ ), 1.04 (t, J=7.5 Hz, 6-n-butylamine-d-Me), 0.93 (m, 7c-n-butylamine-b-CH$_2$), 0.82 (m, 7c-n-butylamine-c-CH$_2$), 0.63 (t, J=6.9 Hz, 7c-n-butylamine-d-Me), −1.26, −1.48 (each br s, NH);

HR mass spectrum: C$_{42}$H$_{54}$N$_6$O$_4$ requires 706.4206; found 706.4194.

EXAMPLE 8

Preparation of Chlorin-p$_6$-6-N$^\epsilon$-Lysylamide-7-Methyl Ester

This example illustrates preparation of chlorin-p$_6$ 6-N$^\epsilon$-lysylamide-7-methyl ester compound (II).

Purpurin-18 methyl ester (3) (30 mg, 0.052 mmole) was dissolved in pyridine (50 mL), to which was added lysine (600 mg, 4 mmole) in water (15 mL) dropwise to make a homogeneous solution. The mixture was stirred at room temperature in the dark under nitrogen for 3 hours. Spectrophotometry showed no remaining starting material. Then the reaction mixture was evaporated to dryness with an oil pump at temperatures below 40° C.

The crude product was dissolved in a minimum amount of water and purified by a C-18 Sep-Pak. cartridge, eluted first with water (100 ml) to remove lysine, then with 80/20 water/methanol (10 mL) to remove some yellow and green impurities, and finally with 20/80 water/methanol to remove the desired green compound. Methanol was partially removed under vacuum before water was then removed by a freeze-dryer to yield 30 mg, (80%) of chlorin-p$_6$ 6-N$^\epsilon$-lysylamide-7-methyl ester (II).

mp>300° C.;

UV $\lambda_{max}$ (MeOH) 660 nm ($\epsilon$ 3.96×10$^4$), 606 (3.92×10$^3$), 528 (3.38×10$^3$), 500 (1.09×10$^4$), 400 (1.45×10$^5$);

LR mass spectrum: 725 (MH+);

Anal. Calcd. for C$_{40}$H$_{48}$N$_6$O$_7$; C, 66.28; H, 6.67; N, 11.59. Found: C, 65.90; H, 6.85; N, 10.92.

EXAMPLE 9

Preparation of Chlorin-p$_6$-6-N$^\epsilon$-Lysylmethoxyamide-7-Methyl Ester

This example illustrates preparation of chlorin-p$_6$ 6-N$^\epsilon$-lysylmethyoxyamide-7-methyl ester (III) or chlorin-p$_6$ $\gamma$-N$^\epsilon$lysylmethoxyamide-7-methyl ester (IV).

Lysine methyl ester dihydrochloride (5.827 g, 25 mmole) was dissolved in water (20 mL), to which was added aqueous sodium hydroxide solution (2.5M, 20 mL). The resulting solution was extracted with chloroform (4×500 mL) and the combined organic layer was evaporated (45° C.) to give a syrup. To this syrup was added purpurin-18 methyl ester (3) (30 mg, 0.052 mmole) in chloroform (20 mL). The mixture was stirred at room temperature in the dark under nitrogen for 3 hours. Spectrophotometry showed no remaining starting material. The reaction mixture was then poured into a solution of methylene chloride (200 mL) and water (100 mL) followed by addition of diluted hydrochloric acid to adjust the aqueous layer to pH~6. The organic layer was separated, washed with water, dried and evaporated to dryness. The product was purified by preparative TLC, eluting with 80/20 methylene chloride /methanol to give chlorin-p$_6$-6-N$^\epsilon$-lysylmethoxyamide-7-methyl ester as major product along with a more polar minor green compound chlorin-p6-N$^\epsilon$-lysylmethoxyamide-7-methyl ester (III).

After crystallization from methylene chloride/n-hexane the mixture yielded 26 mg (70%) of 6-lysylamide (III) and 2.6 mg, (7%) of the $\gamma$ lysylamide (IV).

Physical Data—Compound III mp 185°–186° C.

UV $\lambda_{max}$ (CH$_2$Cl$_2$) 666 nm ($\epsilon$ 4.22×10$^4$), 612 (4.61×10$^3$), 560 (1.76×10$^3$), 530 (4.51×10$^3$), 500 (1.18×10$^4$), 402 (1.33×10$^5$);

$^1$HNMR (300 MHz, CDCl$_3$) $\delta$, ppm, 9.69 (s, $\beta$-meso H), 9.66 (s, $\alpha$-meso H), 8.76 (s, $\delta$-meso H), 8.12 (dd, J=17.7, 11.5 Hz, 2a-H), 6.87 (br t, 6-lysine-CONH), 6.38 (d, J=17.7 Hz, 2b-H), 6.16 (d, J=11.5 Hz, 2b'-H), 5.03 (d, J=8.7 Hz, 7-H), 4.25 (m, 6-lysine-$\epsilon$-CH$_2$), 3.97 (br q, 8-H), 3.76 (q, J=7.5 Hz, 4a-CH$_2$), 3.57 (s, 3H), 3.50 (s, 3H), 3.42 (m, 6-lysine-$\alpha$-H), 3.35 (s, 3H), 2.84 (s, 3H), 2.78 (s, 3H), 2.36, 2.17 (m, 7a & 7b-CH$_2$CH$_2$), 2.05–1.54 (m, 6-lysine-$\beta$, $\gamma$, $\delta$-CH$_2$CH$_2$CH$_2$), 1.74 (br d, 8-Me), 1.72 (br t, J=7.5 Hz, 4b-Me), −1.61, −1.97 (each br s, NH);

LR mass spectrum: 739 (MH+);

Anal. Calcd. for C$_{41}$H$_{50}$N$_6$O$_7$H$_2$O: C, 65.05; H, 6.93; N, 11.11. Found: C, 65.48; H, 6.69; N, 10.77.

Physical Data—Compound (IV).

mp 133°–134° C.

UV $\lambda_{max}$ (CH$_2$Cl$_2$) 666 nm ($\epsilon$ 4.19×10$^4$), 612 (4.42×10$^3$), 530 (4.66×10$^3$), 500 (1.12×10$^4$), 402 (1.35×10$^5$);

$^1$HNMR (300 MHz, CDCl$_3$) $\delta$, ppm, 9.67 (s, $\beta$-meso H), 9.64 (s, $\alpha$-meso H), 8.77 (s, $\delta$-meso H), 8.09 (dd, J=18, 11.5 Hz, 2a-H), 6.69 (br t, $\gamma$-lysine-CONH), 6.36 (d, J=18 Hz, 2b-H), 6.15 (d, J=11.5 Hz, 2b'-H), 5.15 (br d, 7-H), 4.37 (br q, 8-H), 4.00 (m, $\gamma$-lysine-$\epsilon$-CH$_2$),, 3.80 (br q, 4a-CH$_2$), 3.74 ( s, 3H), 3.58 ( s, 3H), 3.55 ( s, 3H), 3.50 (m, $\gamma$-lysine-$\alpha$-H), 3.30 (s, 3H), 3.12 (s, 3H), 2.70-2.50, 2.35-2.10 (m, 7a & 7b-CH$_2$CH$_2$), 2.02-1.50 (br m, $\gamma$-lysine-$\beta$,$\gamma$,$\delta$-CH$_2$CH$_2$CH$_2$), 1.80 (br d, 8-Me), 1.69 (br t, 4b-Me), −1.51, −1.87 (each br s, NH);

LR mass spectrum: 739 (MH+).

EXAMPLE 10

Chlorin-p$_6$-6-N$^\epsilon$-Lysylmethoxyamide-$\gamma$,7-Dimethyl Ester

This example illustrates preparation of chlorin-p$_6$-6-N$^\epsilon$-lysylmethoxyamide-$\gamma$,7-dimethyl ester, compound (V).

Chlorin-p$_6$-6-N$^\epsilon$--lysylmethoxyamide-7-methyl ester (III ) (26 mg, 0. 036 mmole) was first dissolved in a minimum amount of methanol, then diluted with methylene chloride before treated with excess ethereal diazomethane, then washed with water, dried and evaporated to dryness. The product was purified by preparative TLC, eluting with 96/4 methylene chloride/methanol. After crystallization from methylene chloride/n-hexane, the yield was 17 mg (63%) of chlorin-p$_6$-6-N$^\epsilon$-lysylmethoxyamide-$\gamma$,7-dimethyl ester (V) .

mp 108°–109° C.;

UV $\lambda_{max}$ (CH$_2$Cl$_2$) 666 nm ($\epsilon$ 4.71×10$^4$), 610 (4.90×10$^3$), 530 (4.75×10$^3$) 500 (1.29×10$^4$), 402 (1.57×10$^5$);

$^1$HNMR (300 MHz, CDCl$_3$) $\delta$, ppm, 9.71 (s, $\beta$-meso H), 9.61 (s, $\alpha$-meso H), 8.77 (s, d-meso H), 8.03 (dd, J=17.5, 11.5 Hz, 2a-H), 6.36 (t, J=5.7 Hz, 6-lysine-CONH), 6.33 (dd, J=17.5, 1.5 Hz, 2b-H), 6.15 (dd, J=11.5, 1.5 Hz, 2b'-H), 5.04 (d, J=8.7 Hz, 7-H), 4.45 (q, J=7.2 Hz, 8-H), 4.21 (s, 3H), 3.87 (m, 6-lysine-$\epsilon$-H), 3.74

(q, J=7.5 Hz, 4a-CH$_2$), 3.70 (s, 3H), 3.66 (m, 6-lysine-$\epsilon$'-H), 3.61 (s, 3H), 3.48 (m, 6-lysine-$\alpha$-H), 3.45 (s, 3H), 3.44 ($\alpha$, 3H), 3.27 (s, 3H), 2.38 (m, 7b-H), 2.28 (m, 7a-H), 2.04 (m, 7b'-H), 1.96(m, 7a'-H), 1.87 (m, 6-lysine-$\gamma$-CH$_2$), 1.84 ($\delta$, J=7.2 Hz, 8-Me), 1.78 (m, 6-lysine-$\delta$-CH$_2$), 1.70 (t, J =7.5 Hz, 4b-Me), 1.59 (m, 6-lysine-$\beta$-CH$_2$), $-1.32$, $-1.55$ (each br s, NH );

HR mass spectrum: C$_{42}$H$_{52}$N$_6$O$_7$ requires 752.3897; found 752.3861;

Anal. Calcd. for C$_{42}$H$_{52}$N$_6$O$_7$: C, 67.00; H, 6.96; N, 11.16. Found: C, 66.76; H, 7.04; N, 10.80.

EXAMPLE 11

Preparation of Chlorin-p$_6$-$\gamma$-N$^\epsilon$-Lysylmethoxyamide-6,7-Dimethyl Ester This example illustrates preparation of chlorin-p$_6$-$\gamma$-N$^\epsilon$-lysylmethoxyamide-6-7-dimethyl ether (VI).

Chlorin-p$_6$-$\gamma$-N$^\epsilon$-lysylmethoxyamide-7-methyl ester (IV) (2.6 mg, 0.0035 mmole) was first dissolved in a minimum amount of methanol then diluted with methylene chloride and treated with excess ethereal diazomethane, then washed with water, dried and evaporated to dryness. The product was purified by preparative TLC, eluting with 96/4 methylene chloride/methanol. Crystallization from methylene chloride/n-hexane it yielded 1.06 mg (40%) of chlorin-p$_6$-$\gamma$-N$^\epsilon$-lysylmethoxyamide-6,7-dimethyl ester (VI).

mp 129°-130° C.;

UV $\lambda_{max}$ (CHCl$_3$, relative absorbance) 666 nm (30.9), 612 (3.9), 530 (4.3), 500 (8.9), 402 (100);

$^1$HNMR (300 MHz, CDCl$_3$) $\delta$, ppm, 9.74 (s, $\beta$-meso H), 9.58 (s, $\alpha$-meso H), 8.76 (s, $\delta$-meso H), 8.04 (dd, J=17.7, 11.4 Hz, 2a-H), 6.34 (dd, J=17.7, 1.2 Hz, 2b-H), 6.26 (br t, $\gamma$-lysine-CONH), 6.17 (dd, J=11.4, 1.2 Hz, 2b'-H), 5.27 (br d, 7-H), 4.40 (q, J=7.2 Hz, 8-H), 4.22 (s, 3H), 3.96 (m, $\gamma$-lysine-$\epsilon$-H), 3.76 (q, J=7.5 Hz, 4a-CH$_2$), 3.69 (m, $\gamma$-lysine-$\epsilon$'-H), 3.66 (s, 3H), 3.65 (s, 3H), 3.42 (m, $\gamma$-lysine-$\alpha$-H), 3.45 (s, 3H), 3.29 (s, 3H), 3.13 (s, 3H), 2.38-2.28, 2.04-1.96 (m, 7a & 7b-CH$_2$CH$_2$), 1.84 (d, J=7.2 Hz, 8-Me), 1.70 (t, J=7.5 Hz, 4b-Me), 1.87-1.59 (m, $\gamma$lysine-$\beta$, $\gamma$, $\delta$-CH$_2$CH$_2$CH$_2$), $-1.28$, $-1.42$ (each br s, NH);

HR mass spectrum: C$_{42}$H$_{52}$N$_6$O$_7$ requires 752.3897; found 752.3857.

EXAMPLE 12

Preparation of Chlorin-p$_6$-6-N$^\delta$-Ornithylmethoxyamide-$\gamma$,7-Dimethyl Ester This example illustrates preparation of chlorin-p$_6$-6-N$^\delta$-ornithylmethoxyamide-$\gamma$,7-dimethyl Ester.

Ornithine hydrochloride ( 16.8 g, 0.1 mole) was dissolved in water (20 mL), to which was added sodium hydroxide ( 4 g, 0.1 mole) . After completely evaporating the water using a freeze drier, methanol ( 100 mL) was added, and the suspension was stirred at room temperature overnight, then filtered. The clear methanol filtrate was concentrated slowly under vacuum to about 10 mL to a white slurry and solid. The white solid was collected and air dried to give ornithine (9.2 g, 70%).

Ornithine (5 g, 370 mmole) was dissolved in water (2 mL) to which was slowly added pyridine until the moment before ornithine began to precipitate out. Purpurin-18 methyl ester (30 mg, 0.052 mmole) was dissolved in pyridine (5 mL) to which was slowly added water until the moment before purpurin-18 methyl ester began to precipitate out. Then the water-pyridine solution of ornithine was added dropwise over two days to the stirred water-pyridine solution of purpurin-18 methyl ester (3) at room temperature in the dark, avoiding precipitation of either ornithine or purpurin-18 methyl ester by addition of minimum amounts of water or pyridine.

After the addition, the reaction mixture to stirred at 55° C. until spectrophotometry showed no remaining starting material. Then the reaction mixture was evaporated to dryness under oil pump at temperatures below 40° C.

The crude product was dissolved in water and purified by a C-18 Sep-Pak cartridge, eluted first with water to remove ornithine, then with 80/20 water/methanol to remove some yellow and green impurities, and finally with 20/80 water/methanol to remove the desired green compound. Methanol was partially removed under vacuum at temperatures below 40° C. before completely removing water by using a freeze dryer to give chlorin-p$_6$-6-N$^\delta$-ornithyl-amide-7-methyl ester (XI) (7.5 mg, 20%) which was then first dissolved in a minimum amount of methanol and diluted with methylene chloride before being treated with excess ethereal diazomethane. The final product was purified by preparative TLC, eluting with 96/4 methylene chloride/methanol. Evaporation of the solvents yielded 3 mg (8%) of chlorin-p$_6$ 6-N$^\delta$-ornithylmethoxyamide-$\gamma$,7-dimethyl ester (XII).

mp 129°-130° C.;

UV $\lambda_{max}$ (CH$_2$Cl$_2$) 662 nm ($\epsilon$ 4.27$\times$10$^4$), 608 (5.02$\times$10$^3$), 528 (4.52$\times$10$^3$), 498 (1.25$\times$10$^4$), 400 (1.50$\times$10$^2$);

$^1$HNMR (300 MHz, CDCl$_3$) $\delta$, ppm, 9.73 (s, $\beta$-meso H), 9.62 (s, $\alpha$-meso H), 8.76 (s, $\delta$-meso H), 8.05 (dd, J=17.5, 11.7 Hz, 2a-H), 7.10 (t, J=6.6 Hz, 6-ornithine-CONH), 6.34 (dd, J=17.5, 1.2 Hz, 2b-H), 6.16 (dd, J=11.7, 1.2 Hz, 2b'-H), 5.04 (d, J=8.7 Hz, 7-H), 4.44 (q, J=7.2 Hz, 8-H), 4.21 (s, 3H), 3.93 (m, 6-ornithine-$\delta$-H), 3.77 (q, J =7.5 Hz, 4a-CH$_2$), 3.71 (s, 3H), 3.65 (m, 6-ornithine-$\delta$'-H), 3.62 (s, 3H), 3.50 (m, 6-ornithine-$\alpha$-H), 3.46 (s, 3H), 3.44 (s, 3H), 3.29 ( s, 3H), 238-2.27, 2.02-1.94 (m, 7a & 7b-CH$_2$CH$_2$), 1.87-1.69 (m, 6-ornithine-$\beta$, $\gamma$-CH$_2$CH$_2$), 1.83 (d, J=6.9 Hz, 8-Me), 1.71 (t, J=7.5 Hz, 4b-Me), $-1.30$, $-1.55$ (each br s, NH);

HR mass spectrum: C$_{41}$H$_{50}$N$_6$O$_7$ requires 738.3741; found 738.3683.

EXAMPLE 13

Effectiveness of Lysyl Chlorin-p$_6$-Chlorin p6 Mixture in Photodynamic Therapy of the Subcutaneous 9L Glioma in the Rat This example illustrates the use of lysyl-chlorin-p$_6$/chlorin p$_6$-mixture (LCP) for treatment of rat 9L glioma.

Photosensitizer

Lysyl-chlorin-p$_6$ was prepared by treatment of purpurin 18 methyl ester (obtained from chlorophyll-a) with lysine in a mixture of dichloromethane, pyridine, and water. It was purified using a Waters Associate's C18 SepPak cartridge. Reversed phase analytical high-performance liquid chromatography (HPLC) indicated the product to consist of 60% lysyl chlorin-p$_6$ and 40% chlorin-p$_6$ based on equal absorbance at 403 nm. This mixture is termed "LCP". The long wavelength molar extinction coefficient of lysyl-chlorin-p$_6$ in methanol was 39,600 at 660 nm.

LCP in powder form was used for all experiments. The powder was dissolved in phosphate buffered saline (PBS) and 0.1N NaOH (pH 10.0 to 11.0), brought to pH 7.35 with 0.1N HCl, then sterilized with a 0.45 micron filter. Solutions were used the same day as prepared and always protected from light. Absorption spectroscopy and HPLC showed no breakdown of LCP when stored in the dark at 4° C., either when in solution for 24 hours, or when stored in powder form for up to 4 months.

Animal Tumor Model

While under halothane anesthesia, male Fisher 344 rats weighing 160-220 grams, were injected in the left flank with $0.6-2 \times 10^6$ glioma cells suspended in 0.3 ml of RPMI media containing 10% fetal calf serum. Experiments were initiated when tumors were between 14 and 22 mm maximum length or width (between 18 and 27 days after tumor injection). Rats were divided into three groups of 25 to 35 animals each for tumor temperature measurements, evaluation of tumor necrosis 1 day after irradiation, and for tumor regrowth experiments. Within each experiment, rats were further divided into groups of 5 or 6 animals to form individual treatment groups.

Determination of Irradiation Wavelength

Absorption spectra were obtained using a diode array HP 8540A spectrophotometer (Hewlett Packard, Palo Alto, Calif.) from samples of photosensitizer dissolved in PBS at a concentration of 0.04 mg/ml and a pH of 7.4, either with 10% fetal calf serum or with $1 \times 10^6$ 9L glioma cells/mi. The absorption peak of LCP was at 664 nm in both samples, and this wavelength was used for irradiation of rats.

In vivo Light Source and Delivery System

An argon-pumped dye laser system (Spectra Physics 2040 and 375B, Mountain View, Calif.) tuned to emit light at 664 nm was used. A quartz fiber fitted with a microlens (Laser Therapeutics, Inc., Buellton, Calif.) was interfaced to the dye laser to deliver a uniform field of light. Laser output was measured with a power meter (Photodyne, 66XLA, Newbury Park, Calif.). Treatment areas included a minimum of 1 mm of normal tissue adjacent to the tumor.

Photosensitizer Injections and Preparation for Tumor Irradiation

Rats were anesthetized with pentobarbital (45 mg/kg, i.p.) and then injected in the left femoral vein with LCP (2.5 mg/kg). Between 4 and 4.25 hours later rats were again anesthetized with pentobarbital (55 mg/kg, i.p.), placed on a water circulation heating pad maintained at 37° C., and irradiated Tumor Temperature Measurements Temperature profiles as a function of fluence and time were obtained. A 26-gauge hypodermic needle microprobe (Sensortek, Clifton, N.J.) was placed in the tumors perpendicularly to the plane of delivered light 3 mm below the skin surface. Temperature changes were measured within tumors during and immediately after treatment at power densities of 50 and 100 mW/cm². Total irradiation times were 33 minutes 20 seconds, resulting in energy doses of 100 and 200 J/cm², respectively. Controls were rats injected with an equal volume of PBS and similarly irradiated.

PDT Tumor Treatments

Rats were irradiated at a power density of 50 MW/cm² with total laser energy densities of 25, 50, and 100 J/cm². Irradiation times were 8 minutes 20 seconds, 16 minutes 40 seconds and 33 minutes 20 seconds, respectively, per animal. Controls were rats which were either not injected or irradiated, injected with photosensitizer but not irradiated, or injected with an equal volume of PBS and irradiated at 100 J/cm².

Histologic Examination 1 Day Post Irradiation

Animals were euthanized 24 hours after completion of irradiation and immediately necropsied. Tissues were evaluated after immersion fixation in 10% neutral buffered formalin, routine processing, sectioning, and then staining with hematoxylin and eosin (H&E). Morphometric determination of tumor necrosis was done by examining sections from 2 blocks of tumor tissue cut perpendicular to the skin surface and taken at 90° C. angles to one another, using a 42 point grid (Graticules, Ltd., Kent, England). Percent tumor necrosis was calculated as follows:

$$\frac{\frac{Pn_1}{Pn_2 + Pv_1} + \frac{Pn_2}{Pn_2 + Pv_2}}{2} \times 100$$

where:

$Pn_1$ = number of points over necrotic tumor, section from first block;

$Pn_2$ = number of points over necrotic tumor, section from second block;

$Pv_1$ = number of points viable tumor, section from first block;

$Pv_2$ = number of points over viable tumor, section from second block.

PDT-mediated Inhibition of Tumor Regrowth

Tumors were monitored every 2 days until tumor volume had increased six fold over measurements made immediately pretreatment. Tumor size was calculated as (A) (B) (C) ($\pi/6$) as described in *Cancer Res.*, 50:3985 (1990).

PDT-mediated Skin Response

Skin changes in rats used for tumor regrowth experiments were evaluated within the irradiated areas overlying tumors, the ears, and the feet using a quantitative scoring system (described in Table 4) to document the degree of skin damage induced by each treatment and by normal fluorescent room light. Evaluation of the skin was made daily. The score given to each animal represents the most severe reaction (the highest score) seen in that animal during the experiment.

Statistical Analysis

Individual group means from the percent tumor necrosis and tumor regrowth following PDT experiments were compared to the group receiving no injection or light, using the Wilcoxon 2-sample test, normal approximation, with continuity correction of 0.5.

TABLE 4

| Score | Observation |
|---|---|
| \multicolumn{2}{l}{Grading System for Skin Photosensitization Reaction} |
| Reaction | |
| 0 | Normal |
| 1 | Edema |
| 2 | Erythema |
| 3 | Small area of necrosis, <3 mm in diameter |
| 4 | Moderate area of necrosis, 3-10 mm in diameter |
| 5 | Patchy area of necrosis >10 mm in diameter |
| 6 | Complete necrosis of skin >15 mm in diameter |

What is claimed is:

1. A compound of the formula

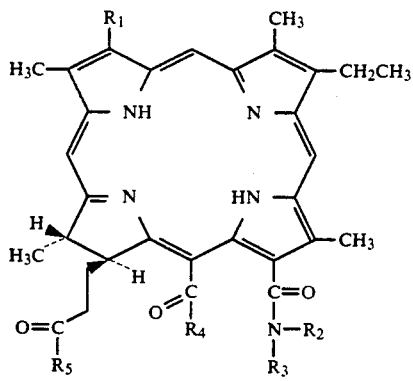

(IA)

wherein
$R_1$ is H; $CH_3$; $CH_2CH_3$; $CH=CH_2$; $CH(OH)CH_3$; $CH(O\text{-alkyl})CH_3$; $C(=O)CH_3$; CHO; $CH_2OH$ or $CH_2$ alkoxy;
$R_2$ is H, alkyl or aryl;
$R_3$ is H; alkyl; aryl; $(CH_2)_n CH(NH_2)CO_2H$ wherein n is 3 or 4; aryl substituted on aromatic ring with alkyl; alkyl substituted with $N(\text{alkyl})_2$ or $^{(+)}N(\text{alkyl})_3$; or $(CH_2)_n CO_2 R_9$ wherein $R_9$ is H, alkyl or aryl;
$R_4$ is OH or alkoxy;
$R_5$ is OH; $OR_{10}$ wherein $R_{10}$ is alkyl or aryl; $NR_{12}R_{13}$ wherein $R_{12}$ and $R_{13}$ are H, alkyl or aryl; or $NH(CH_2)_n CH(NH_2)CO_2H$ wherein n is 3 or 4;
and the pharmaceutically acceptable salts and esters thereof.

2. A compound of the formula

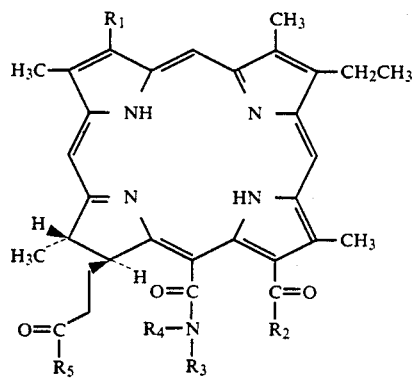

(IB)

wherein
$R_1$ is H; $CH_3$; $CH_2CH_3$; $CH=CH_2$; $CH(OH)CH_3$; $CH(O\text{-alkyl})CH_3$; $C(=O)CH_3$; CHO; $CH_2OH$ or $CH_2$-alkoxy;
$R_2$ is OH or alkoxy;
$R_3$ is H; alkyl or aryl;
$R_4$ is H; alkyl, aryl; $(CH_2)_n CH(NH_2)CO_2H$ wherein n is 3 or 4; aryl substituted on aromatic ring with alkyl; alkyl substituted with $N(\text{alkyl})_2$ or $N(\text{alkyl})_3$; or $(CH_2)_n CO_2 R_9$ wherein $R_9$ is H, alkyl or aryl;
$R_5$ is OH; $OR_{10}$ wherein $R_{10}$ is alkyl or aryl; $NR_{12}R_{13}$ wherein $R_{12}$ and $R_{13}$ are H, alkyl or aryl; or $NH(CH_2)_n CH(NH_2)CO_2H$ wherein n is 3 or 4;
and the pharmaceutically acceptable salts and esters thereof.

3. A method for tumor localization and treatment by photosensitization comprising the steps of:
(a) administering to a person in need of such treatment a compound of the formula

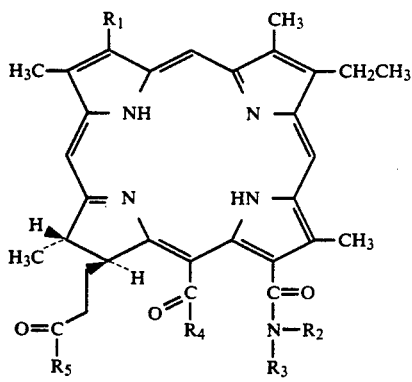

(IA)

wherein
$R_1$ is H; $CH_3$; $CH_2CH_3$; $CH=CH_2$; $CH(OH)CH_3$; $CH(O\text{-alkyl})CH_3$; $C(=O)CH_3$; CHO; $CH_2OH$ or $CH_2$-alkoxy;
$R_2$ is H; alkyl; or aryl;
$R_3$ is H; alkyl; aryl; $(CH_2)_n CH(NH_2)CO_2H$ wherein n is 3 or 4; aryl substituted on the aromatic ring with alkyl; alkyl substituted with $N(\text{alkyl})_2$ $N(\text{alkyl})_3$; or $(CH_2)_n CO_2 R_9$ wherein $R9$ is H, alkyl or aryl;
$R_4$ is OH; or alkoxy;
$R_5$ is OH; $OR_{10}$ wherein $R_{10}$ is alkyl or aryl; $NR_{12}R_{13}$ wherein $R_{12}$ and $R_{13}$ are H, alkyl or aryl; or $NH(CH_2)_n CH(NH_2)CO_2H$ wherein n is 3 or 4; or a pharmaceutically acceptable salt or ester thereof; and
(b) activating the compound of step (a) or appropriate salt or ester thereof with a light between 600–800 nm at an energy density between 25–100 J/cm² for 5–35 minutes.

4. A method for tumor localization and treatment by photosensitization comprising the steps of:
(a) administering to a person in need of such treatment a compound of the formula

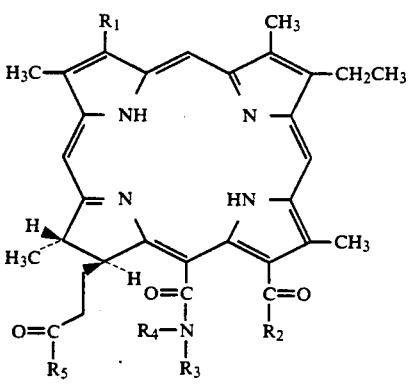

(IB)

wherein
$R_1$ is H, $CH_3$, $CH_2CH_3$, $CH=CH_2$, $CH(OH)CH_3$, $CH(O\text{-alkyl})CH_3$, $C(=O)CH_3$, CHO, $CH_2OH$, or $CH_2$alkoxy;
$R_2$ is OH, or alkoxy;
$R_3$ is H, alkyl, aryl,
$R_4$ is H, alkyl, aryl, $(CH_2)_n CH(NH_2)CO_2H$ wherein n is 3 or 4; aryl substituted on aromatic ring with alkyl; alkyl substituted with N(alkyl)$_2$ or N(alkyl)$_3$; or (CH$_2$)$_n$CO$_2$R$_9$ wherein R$_9$ is H, alkyl or aryl;

R$_5$ is OH; OR$_{10}$ wherein R$_{10}$ is alkyl or aryl; NR$_{12}$R$_{13}$ wherein R$_{12}$ and R$_{13}$ are H, alkyl or aryl; or NH(CH$_2$)$_n$CH(NH$_2$)CO$_2$H wherein n is 3 or 4; or the pharmaceutically acceptable salt and ester thereof; and (b) activating the compound of step (a) or appropriate salt or ester thereof with a light between 600–800 nm at an energy density between 25–100 J/cm$^2$ for 5–35 minutes.

5. A compound of the formula

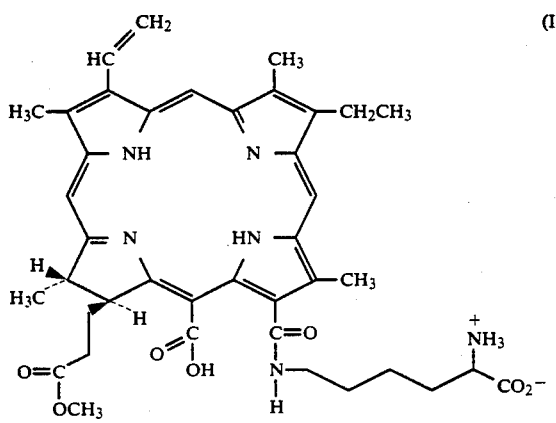

namely, chlorin-p$_6$-6-N$^e$-lysylamide-7-methyl ester.

6. The method of claim 3 comprising the steps of:

(a) administering to a person in need of photosensitization treatment about 2.5 mg/kg of body weigh of a compound of formula

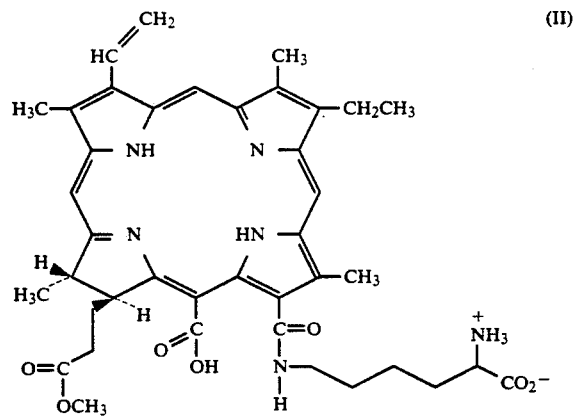

(b) and activating the compound of step (a) with a light between 600–800 nm at an energy density between 25–100 J/cm$^2$ for 5–35 minutes.

7. A compound of the formula

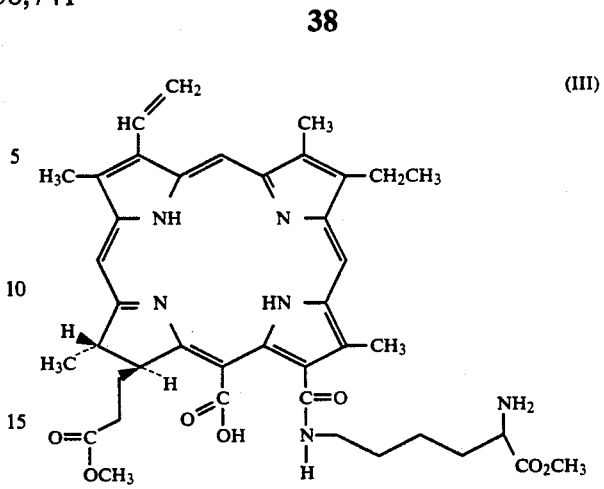

namely, chlorin-p$_6$-N$^e$-lysyl-methoxyamide-7-methyl ester.

8. The method of claim 3 comprising the steps of:

(a) administering to a person in need of photosensitization treatment about 2.5 mg/kg of body weigh of a compound of formula

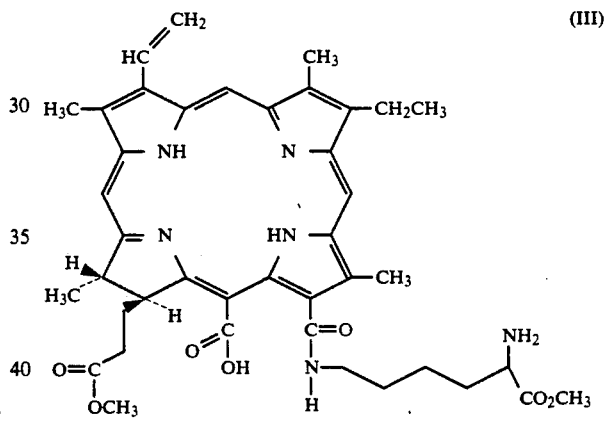

(b) and activating the compound of step (a) with a light between 600–800 nm at an energy density of between 25–100 J/cm$^2$ for 5–35 minutes.

9. A compound of the formula

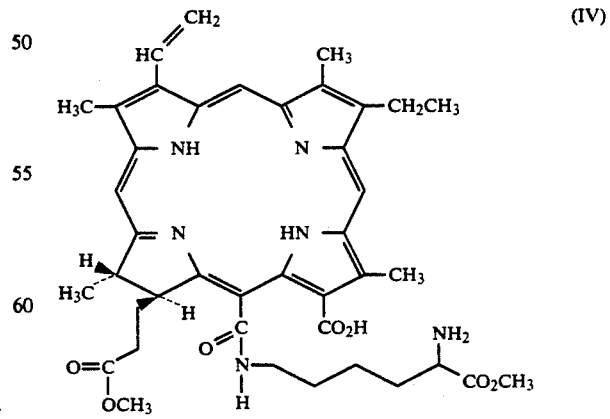

namely, chlorin-p$_6$-γ-N$^e$-lysyl-methoxyamide-7-methyl ester.

10. The method of claim 4 comprising the steps of:

(a) administering to a person in need of photosensitization treatment about 2.5 mg/kg of body weigh of a compound of the formula

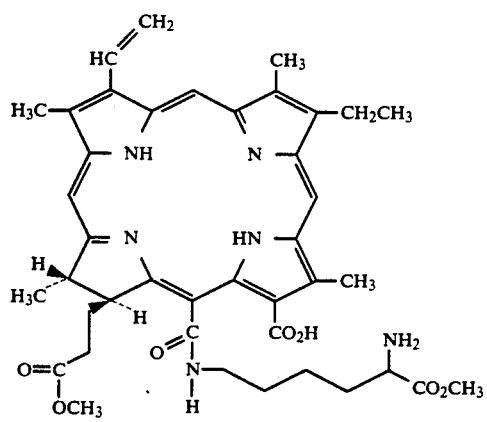

(IV)

(b) and activating the compound of step (a) with a light between 600–800 nm at an energy density between 25–100 J/cm² for 5–35 minutes.

11. A compound of the formula

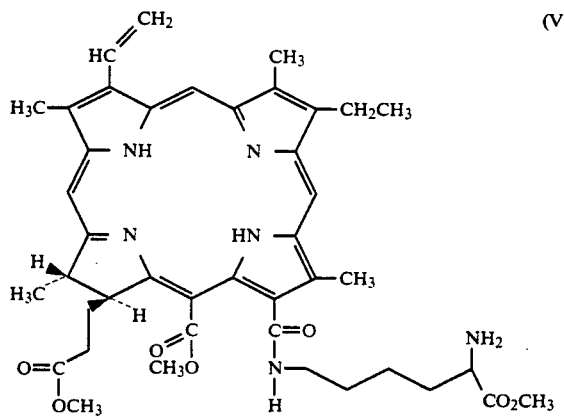

(V)

namely, chlorin-p$_6$-6-N$^e$-lysylmethoxyamide-γ, 7-dimethyl ester.

12. The method of claim 3 comprising the steps of:
(a) administering to a person in need of photosensitization treatment about 2.5 mg/kg of body weight a compound of formula

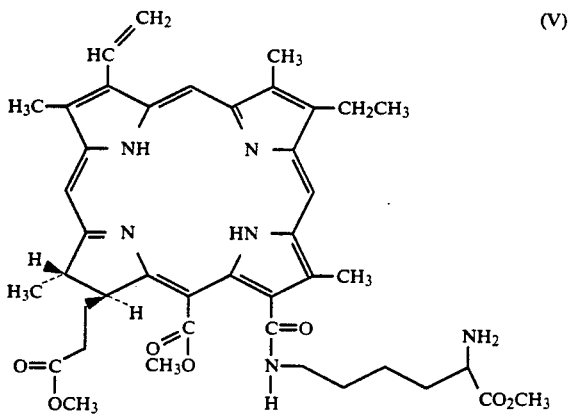

(V)

(b) activating the compound of step (a) with a light between 600–800 nm at an energy density between 25–100 J/cm² for 5–35 minutes.

13. A compound of claim 2 having the formula

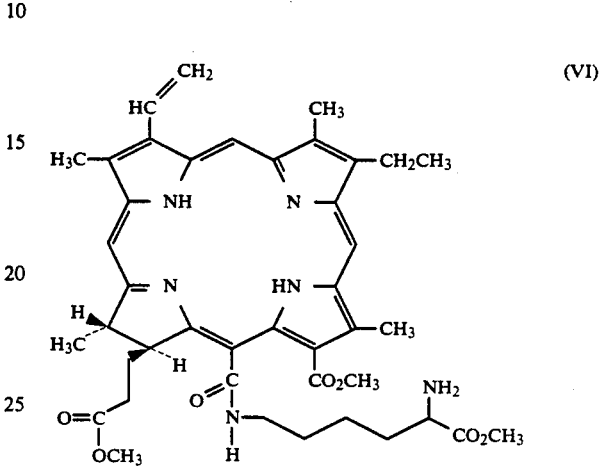

(VI)

namely, chlorin-p$_6$-γ-N$^e$-lysylmethoxyamide-6, 7-dimethyl ester.

14. The method of claim 4 comprising the steps of:

(a) administering to a person in need of photosensitization treatment about 2.5 mg/kg of body weigh of a compound of formula

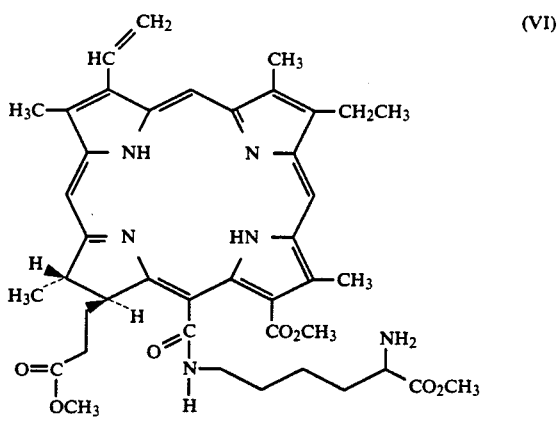

(VI)

(b) activating the compound of step (a) with a light between 600–800 nm at an energy density between 25–100 l/cm² for 5–35 minutes.

15. A compound of the formula

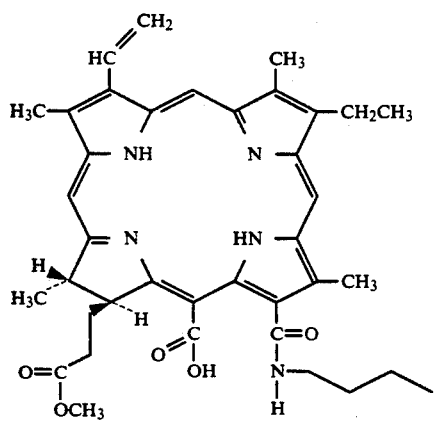

namely, chlorin-p₆-6-N-butylamide-7-methyl ester.

16. The method of claim 3 comprising the steps of:
(a) administering to a person in need of photosensitization treatment about 2.5 mg/kg of body weigh of a compound of the formula

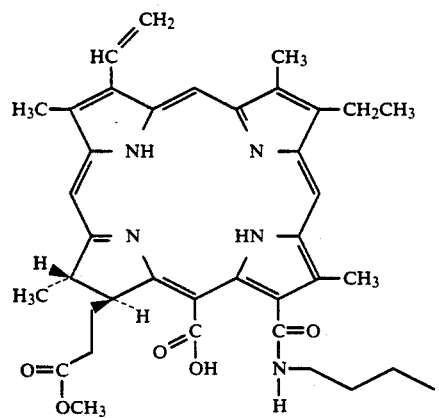

(b) activating the compound of step (a) with a light between 600-800 nm at an energy density between 25-100 J/cm² for 5-35 minutes.

17. A compound of the formula

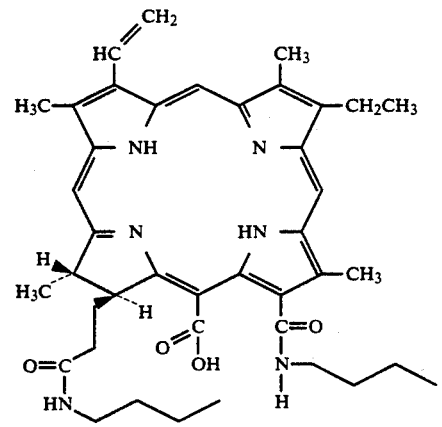

namely, chlorin-p₆-6, 7-di-N-butylamide.

18. The method of claim 4 comprising the steps of:

(a) administering to a person in need of photosensitization treatment about 2.5 mg/kg of body weigh of a compound of formula

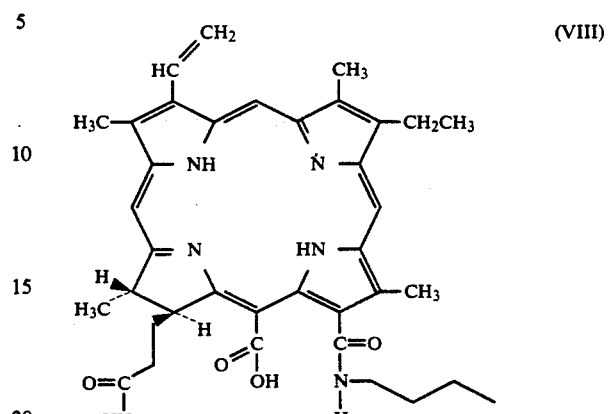

(b) and activating the compound of step (a) with a light between 600-800 nm at an energy density between 25-100 J/cm² for 5-35 minutes.

19. A compound of the formula

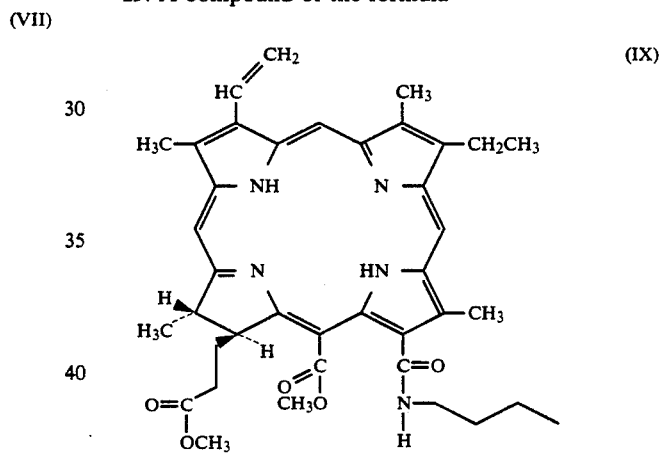

namely, chlorin-p₆-6-N-butylamide-γ-7-dimethyl ester.

20. The method of claim 3 comprising the steps of:
(a) administering to a person in need of photosensitization treatment about 2.5 mg/kg of body weight a compound of formula

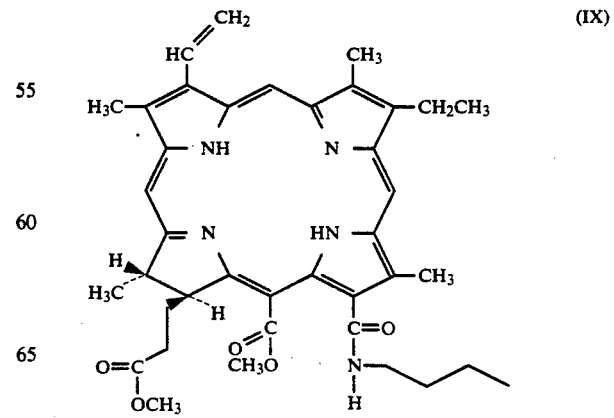

(b) and activating the compound of step (a) with a light between 600–800 nm at an energy density between 25–100 J/cm² for 5–35 minutes.

21. A compound of the formula

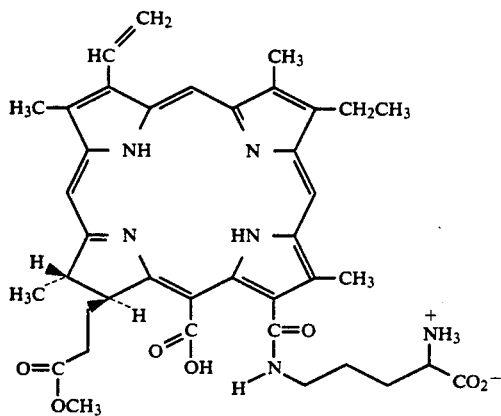

(XI)

namely, chlorin-p₆-6-N, γ-ornithylamide-7-methyl ester.

22. The method of claim 3 comprising the steps of:
(a) administering to a person in need of photosensitization treatment about 2.5 mg/kg of body weight a compound of formula

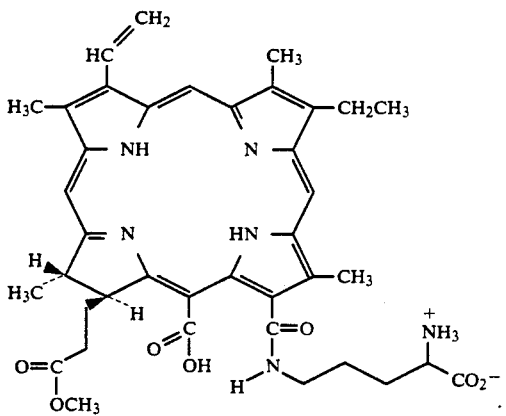

(XI)

(b) activating the compound of step (a) with a light between 600–800 nm at an energy density between 25–100 J/cm² for 5–35 minutes.

23. A compound of the formula

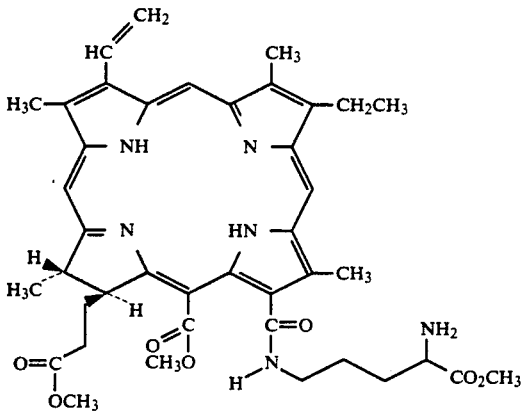

(XII)

namely, chlorin-p₆-6-N-ornithylmethoxyamide-γ-7-dimethyl ester.

24. The method of claim 3 comprising the steps of:
(a) administering to a person in need of photosensitization treatment about 2.5 mg/kg of body weight a compound of the formula

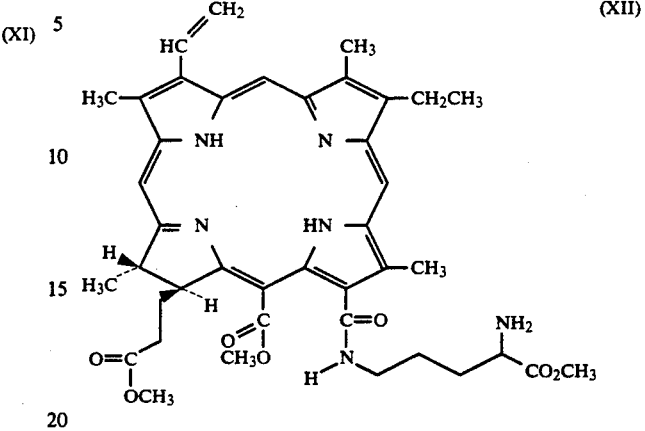

(XII)

(b) and activating the compound of step (a) with a light between 600–800 nm at an energy density between 25–100 J/cm² for 5–35 minutes.

25. A compound of claim 1 having the formula

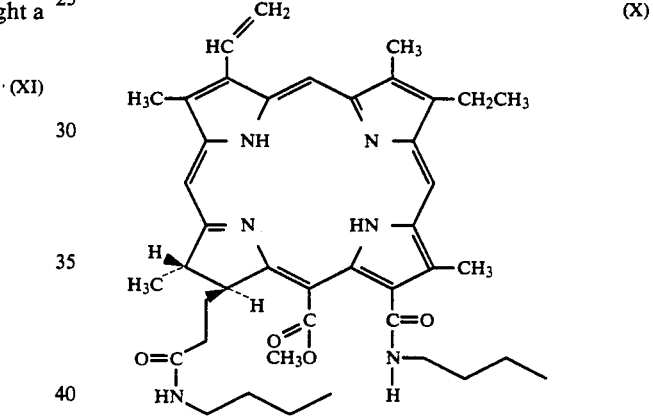

(X)

namely, chlorin-p₆-6-N, di-N butylamide-γ-methyl ester.

26. The method of claim 3 comprising the steps of:
(a) administering to a person in need of photosensitization treatment about 2.5 mg/kg of body weight a compound of formula

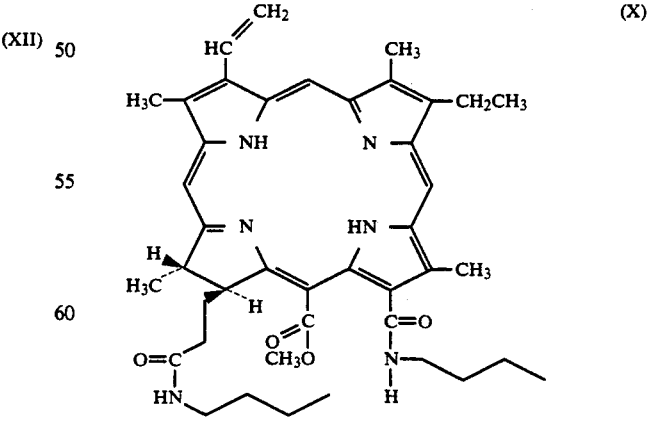

(X)

(b) activating the compound of step (a) with a light between 600–800 nm at an energy density between 25–100 J/cm² for 5–35 minutes.

* * * * *